(12) United States Patent
Deveney et al.

(10) Patent No.: US 6,531,096 B1
(45) Date of Patent: Mar. 11, 2003

(54) METHOD AND APPARATUS FOR AUTOMATICALLY OPENING AND CLOSING VIAL LIDS

(75) Inventors: Thomas W. Deveney, Brownsmill, NJ (US); Ralph J. Brooks, Langhorne, PA (US)

(73) Assignee: Capitol Vial, Inc., Auburn, AL (US)

( * ) Notice: Subject to any disclaimer, the term of this patent is extended or adjusted under 35 U.S.C. 154(b) by 0 days.

(21) Appl. No.: 09/166,985

(22) Filed: Oct. 6, 1998

Related U.S. Application Data
(60) Provisional application No. 60/061,172, filed on Oct. 6, 1997.

(51) Int. Cl.[7] .............................. G01N 35/10; B67B 7/18
(52) U.S. Cl. ......................... 422/65; 422/63; 422/100; 422/104; 436/43; 436/47; 436/49; 436/180; 81/3.2; 81/3.31; 81/3.32
(58) Field of Search ........................... 422/63, 65, 100, 422/104; 436/43, 47, 49, 180; 81/3.2, 3.31, 3.33; 222/562, 565; 220/260, 264; 215/236; 53/381.1

(56) References Cited

U.S. PATENT DOCUMENTS

| | | |
|---|---|---|
| 2,814,404 A | 11/1957 | Towns |
| 3,282,477 A | 11/1966 | Henchert |
| 3,470,930 A | 10/1969 | Jurczenia |
| 3,592,349 A | 7/1971 | Baugh |
| 3,628,405 A * | 12/1971 | Fleisher ...................... 81/3.42 |
| 3,786,982 A | 1/1974 | Rakes et al. |
| 3,900,550 A | 8/1975 | Oliver et al. |
| 4,070,854 A * | 1/1978 | Marino ...................... 53/381.4 |
| 4,377,247 A | 3/1983 | Hazard et al. |
| 4,455,280 A * | 6/1984 | Shinohara et al. .......... 141/154 |
| 4,515,286 A * | 5/1985 | Ushikubo ................... 220/314 |
| 4,655,363 A | 4/1987 | Neat |
| 4,713,219 A | 12/1987 | Gerken et al. |
| 4,717,034 A | 1/1988 | Mumford |
| 4,773,285 A * | 9/1988 | Dionne ........................ 81/3.2 |
| 4,783,056 A | 11/1988 | Abrams et al. |
| 4,807,425 A | 2/1989 | Abrams et al. |
| 4,812,116 A | 3/1989 | Abrams et al. |
| 4,813,570 A | 3/1989 | Pontoppidan |
| 4,860,907 A | 8/1989 | Sondal |
| 4,876,926 A * | 10/1989 | Muszak ....................... 81/3.2 |
| 4,982,553 A * | 1/1991 | Itoh ............................ 53/246 |
| 5,008,082 A * | 4/1991 | Shaw .......................... 422/65 |

(List continued on next page.)

FOREIGN PATENT DOCUMENTS

WO PCT/US93/12490 12/1993

OTHER PUBLICATIONS

Prior art described in the applicant's "Second Supplemental Information Disclosure Statement" dated Nov. 13, 2000.
Notification of Transmittal of International Preliminary Examination Report and International Preliminary Examinations report (Total 4 pages), Aug. 27, 1999.

*Primary Examiner*—Jill Warden
*Assistant Examiner*—Kathryn Bex

(57) ABSTRACT

An apparatus and method for opening a vial lid with respect to its respective container includes the lid having a tamper evident tape applied over a top surface of the lid with the ends of the tape being adhered against the outer side walls of the vial container below a juncture of the lid and the container outer wall. The tape has a score on each side in the area adjacent to the juncture. The apparatus includes a device for opening the lid by lifting the lid with respect to the container by a sufficient elevation to ensure that the tape score is substantially completely separated. A second device places a downwardly depending flange of the lid in an overlapped position with respect to an upper end wall of the container after the lid has been opened.

19 Claims, 20 Drawing Sheets

U.S. PATENT DOCUMENTS

| | | |
|---|---|---|
| 5,012,941 A | 5/1991 | Abrams et al. |
| 5,020,683 A | 6/1991 | Strassheimer |
| 5,108,029 A | 4/1992 | Abrams et al. |
| 5,133,470 A | 7/1992 | Abrams et al. |
| 5,169,374 A | 12/1992 | Abrams et al. |
| 5,199,635 A | 4/1993 | Abrams et al. |
| 5,219,320 A | 6/1993 | Abrams et al. |
| 5,255,574 A * | 10/1993 | Wuerschum .................. 81/3.2 |
| 5,269,430 A | 12/1993 | Schlaupitz et al. |
| 5,271,897 A * | 12/1993 | Wurschum et al. ........... 422/63 |
| 5,289,930 A * | 3/1994 | Inouye ....................... 215/235 |
| 5,429,699 A | 7/1995 | Abrams et al. |
| 5,441,150 A | 8/1995 | Ma |
| 5,474,177 A | 12/1995 | Abrams et al. |
| 5,481,946 A * | 1/1996 | Nishikawa et al. ........... 81/3.2 |
| 5,513,768 A | 5/1996 | Smith |
| 5,575,399 A | 11/1996 | Intini |
| 5,624,528 A | 4/1997 | Abrams et al. |
| 5,628,962 A * | 5/1997 | Kanbara et al. .............. 422/65 |
| 5,667,094 A | 9/1997 | Rapchak et al. |
| 5,723,085 A | 3/1998 | Abrams et al. |

* cited by examiner

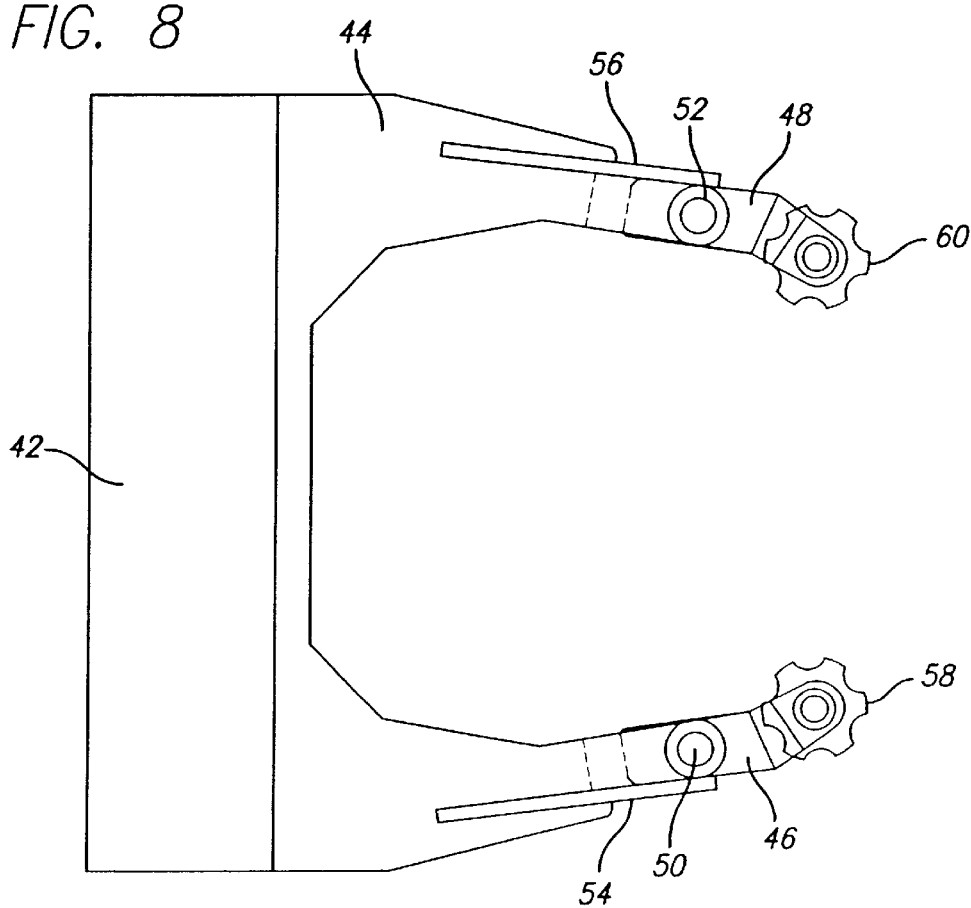
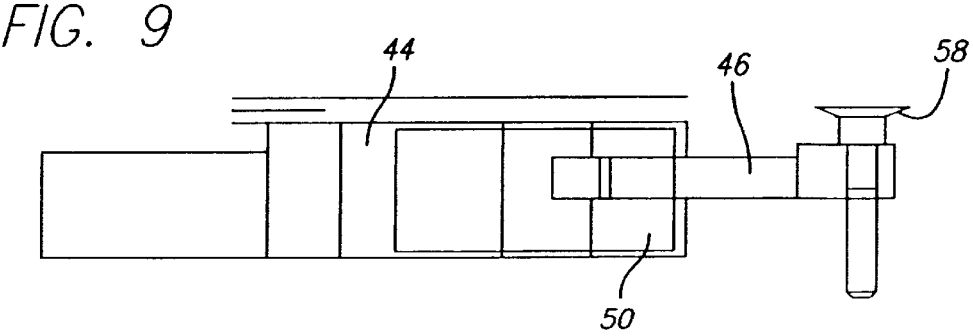

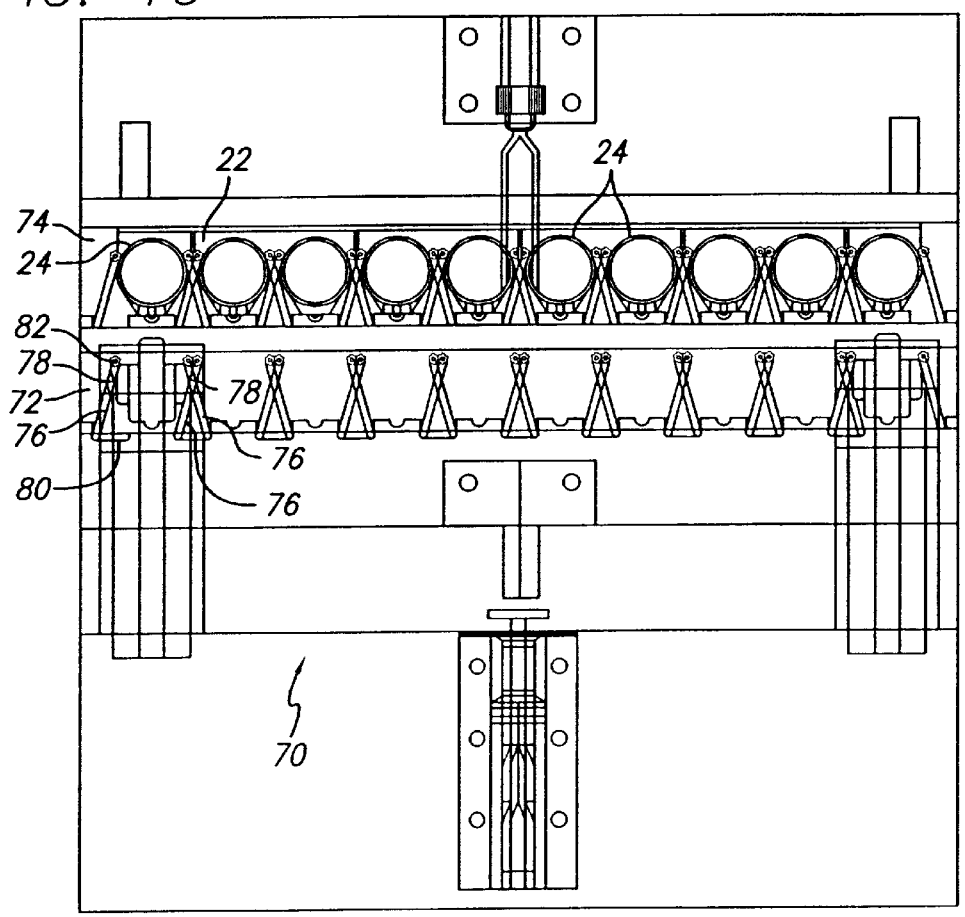
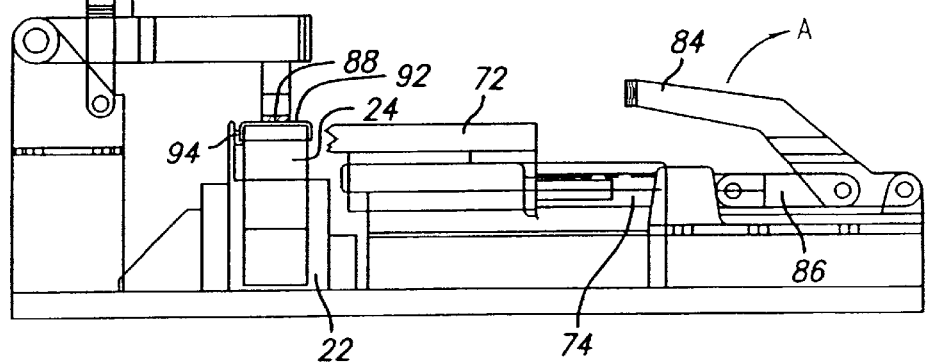

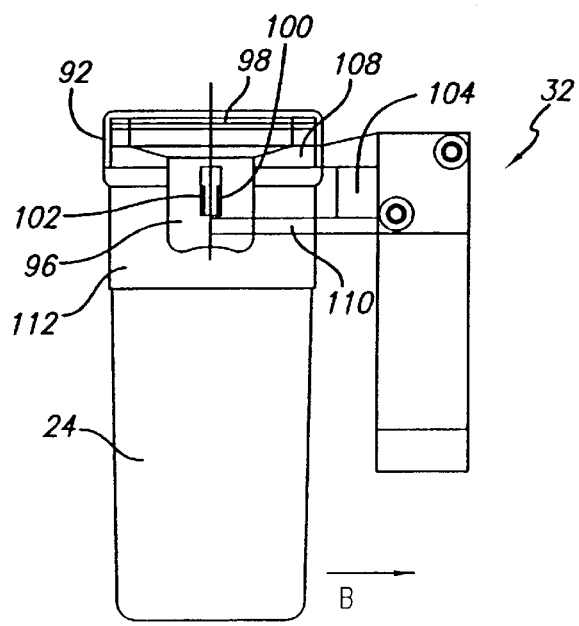
FIG. 12
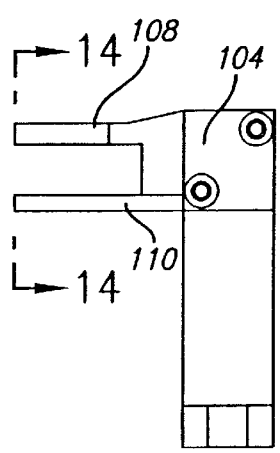
FIG. 13
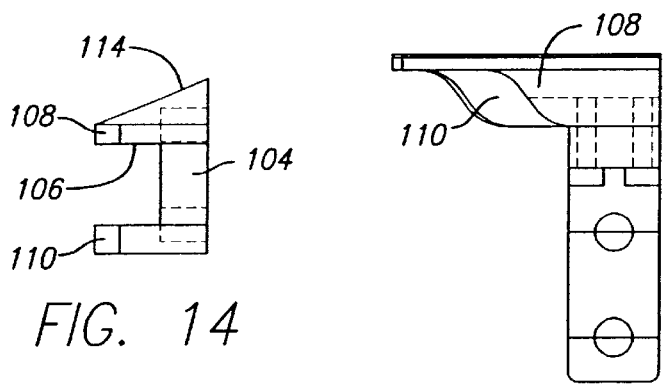
FIG. 14
FIG. 15
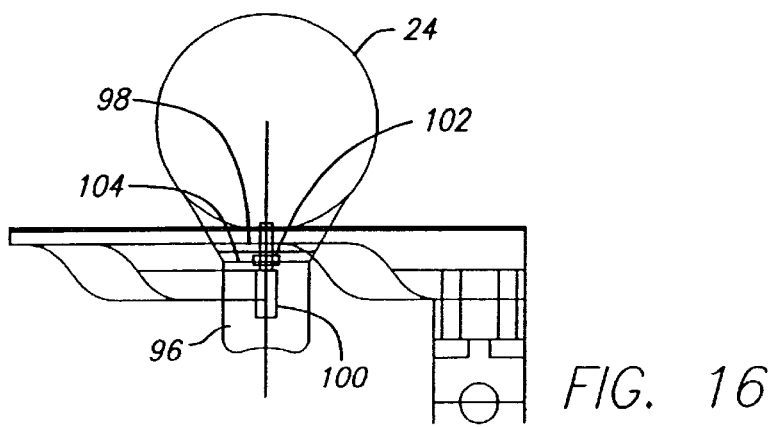
FIG. 16

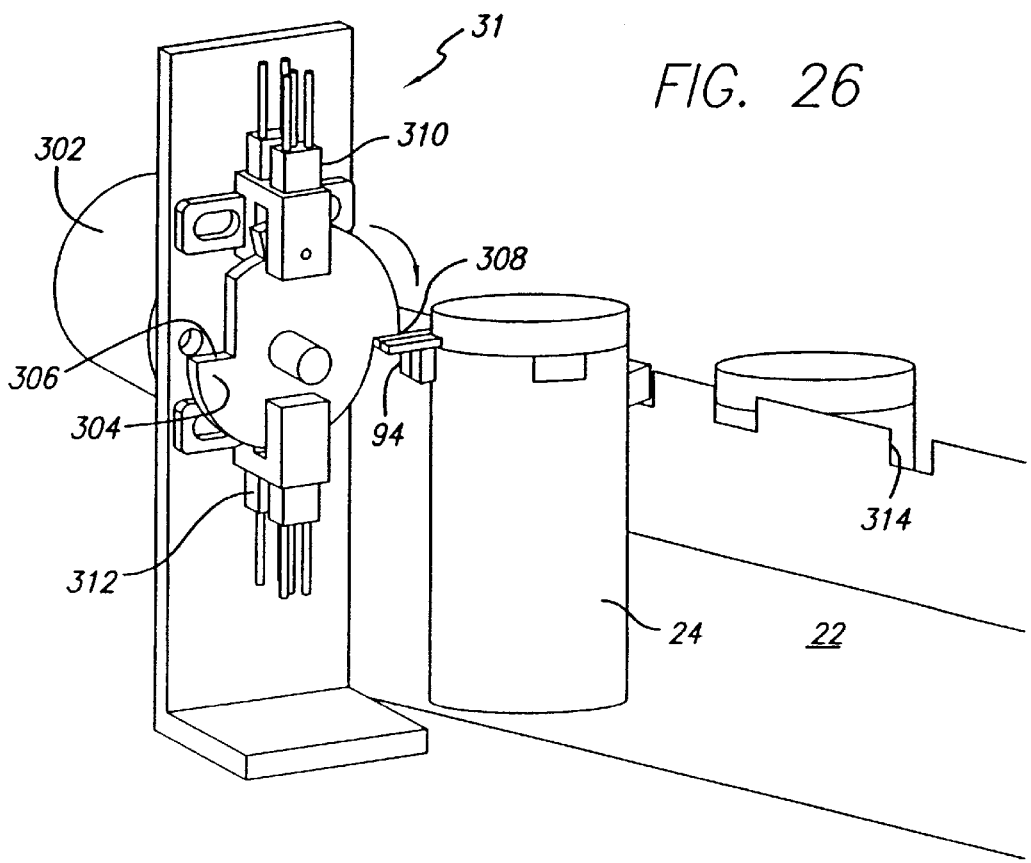
FIG. 26
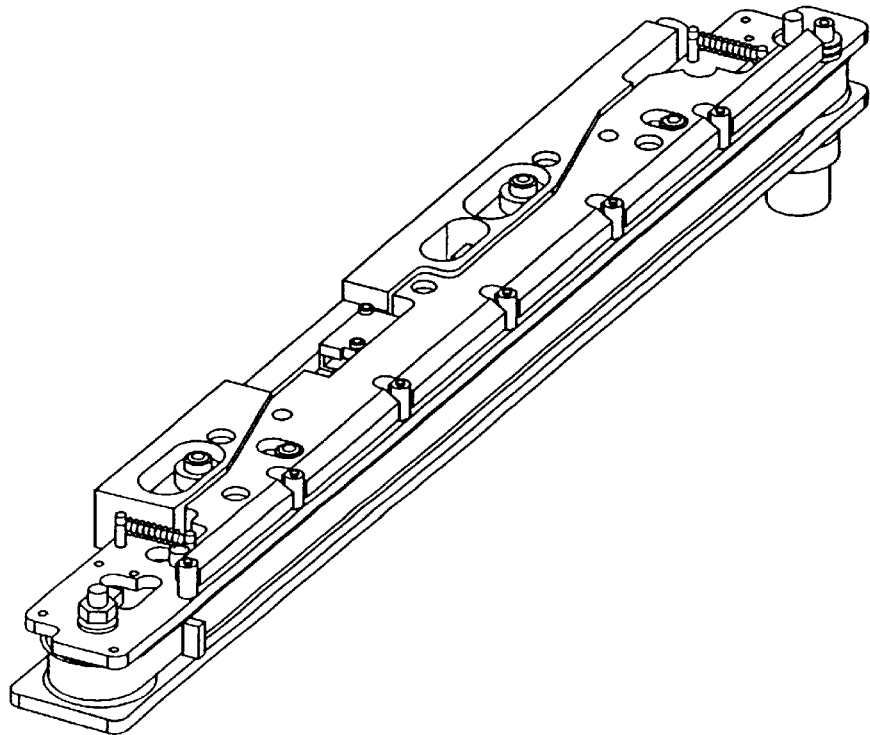

METHOD AND APPARATUS FOR AUTOMATICALLY OPENING AND CLOSING VIAL LIDS

RELATED APPLICATIONS

This application is related to Provisional Application Ser. No. 60/061,172 filed Oct. 6, 1997.

FIELD OF THE INVENTION

The present invention relates to a method and apparatus for automatically opening and closing the lid of a vial. More specifically, the present invention relates to a method and apparatus for automatically opening and closing a vial lid so that liquid contained therein can be transferred to a testing container.

BACKGROUND OF THE INVENTION

Bodily fluids, such as, for example, urine or blood, are analyzed for many purposes. These include, for example, screening for the presence of deleterious or illegal substances, such as, for example, alcohol or illegal drugs, such as marijuana, cocaine, etc., or to test for health reasons, such as to determine cholesterol levels, sugar levels, etc. The test liquid is typically deposited by a test subject in a specimen vial. All or a portion of the liquid is conventionally transferred from the specimen vial to a testing vial by manually pouring liquid from the specimen vial into the testing vial. Alternatively, pipettes have been used to aspirate blood from the specimen vial and, thereafter, dispense that blood into the testing vial. The testing vial is then placed in a testing rack and is tested in a conventional manner.

After a sample vial is filled with fluid (e.g., blood or urine), the lid of the vial is snapped shut to an air and liquid tight closed position. Additionally, any latch, which may be provided on the lid, is pivoted to an engaged or latched position with respect to a tab projecting outwardly on the outer surface of the container. Thereafter, for some applications, a tamper evident tape is typically applied over the top surface of the lid, and the ends of the tape are pressed down and adhered against the outer side walls of the container. Thus, the integrity of the tape provides evidence that the initial seal of the container, after sample collection, has not been compromised. The tape is not to be torn until just prior to the time of testing. Subsequently, the tape must be separated, preferably near the juncture of the vial lid and the container top wall, to open the lid initially.

The transfer of the liquid from the sample vial to the testing vial must maintain sample and data integrity and be conducted with care to ensure the accuracy of the testing results. In other words, the sample and testing vial for each individual specimen must not be cross-contaminated with any other specimen or testing vial.

Currently, there is no automated process for automatically opening a hinged sample vial so that the liquid contained therein can be transferred to a testing vial. One of the reasons for the lack of any automated systems is because the risk of cross-contamination between any two or more specimens must be avoided.

SUMMARY OF THE INVENTION

Accordingly, in one embodiment, the present inventors have found it advantageous to pre-score the tamper proof tape in an area adjacent to the junction line between the lid and the container before opening the lid. Alternatively, the tape may be provided with a pre-score or pre-perforation. However, this has not become the industry practice because, in practice, it requires precision in the field by the users to place the tape in a proper position on the vial so that the pre-scored perforations in the tape align with the juncture between the lid and the container. By pre-scoring the tape a relatively lower force is required to open the container.

The present inventors have also discovered that, on some occasions, a pressure difference exists between the hermetically sealed volume within the container and the ambient atmosphere at the testing site. The pressure difference can be created, for example, by temperature differences and/or atmospheric pressure differences between the sample site and the testing site. These pressure differences can cause the liquid within the container to atomize upon opening. Thus, in one embodiment, the present inventors have found it desirable to open the container only partially, to the extent necessary to cut the tape, and, thereafter, maintain the downwardly depending flange of the container lid in an overlapped position (the lid overlapped position) with respect to the upper cylindrical end wall of the container. The container is thereby vented to the ambient atmosphere to equalize the pressure therein and the spraying or atomization effect is greatly reduced. This also reduces or eliminates the risk of cross-contamination.

In another embodiment, the present inventors have also found it desirable to only open one specimen vial at a time and to maintain any previously opened specimen vials in the lid overlapped position during any indexing movement of the vials to further reduce the risk of cross-contamination.

In accordance with one embodiment of the present invention demonstrating further features, objects and advantages of the present invention, an apparatus and method for opening a vial lid with respect to its respective container includes the lid having a tamper evident tape applied over a top surface of the lid with the ends of the tape being adhered against the outer side walls of the vial container below a juncture of the lid and the container outer wall. The tape has a score on each side in the area adjacent to the juncture. In one embodiment, the apparatus includes a device for opening the lid by lifting the lid with respect to the container by a sufficient elevation to ensure that the tape score is substantially completely separated. A second device places a downwardly depending flange of the lid in an overlapped position with respect to an upper end wall of the container after the lid has been opened.

In a further embodiment, the present invention relates to an apparatus comprising: (a) an orientation device for situating a vial container to a predetermined position in preparation for a lid of the vial container to be opened, the vial container having an opening at its upper end for containing a liquid and a lid attached to one portion of the upper end of the vial container by a hinge, the vial lid having a latch with an aperture and the vial container having an outwardly projecting post wherein the apparatus of the latch fits around the post thereby securing the lid onto the vial container in a closed position; (b) a latch opening device for separating the latch from the post thereby placing the latch in an opened position; and (c) a lid opening device for situating the lid of the vial container to a first predetermined upper limit position.

In another embodiment, the apparatus has a lid pivoting device for opening the lid to a second position to allow transfer of the liquid within the vial container. In a further embodiment, the apparatus has a rack brake device and a plurality of racks containing a plurality of vial containers. The rack brake device comprises a motor which drives a lead screw which drives a pair of opposing ranges to secure the racks in place. The motor can run in reverse to release the brake. In still a further embodiment, the apparatus can have conveyers for moving the vial container from the orientation device to the latch opening devices and to the lid opening devices.

In another embodiment, the present invention relates to a method for automatically opening and closing lids of a vial container. The method comprises the steps of: (a) orientating the vial container to a predetermined position in preparation for the lid of the container to be opened, the vial container having an opening at its upper end for containing a liquid and a lid attached to one position of the upper end of the vial container by a hinge, the lid having a latch with an aperture and the vial container having an outwardly projecting post wherein the aperture of the latch fits the post thereby securing the latch in a closed position; (b) separating the latch from the post thereby placing the latch in an opened position; and (c) opening the lid to a first predetermined upper limit position. In a further embodiment, the method comprises the step of opening the lid to a second position to allow transfer of the liquid.

In still a further embodiment, the method comprises closing the lid onto the container after transfer of the liquid. In yet another embodiment, the vial container has a tape adhered over the lid and overlapped against outer side walls of the container and the method further comprises pre-scoring the tape before orientating the vial container. In still another embodiment, step (c) further includes separating the prescored tape during opening the lid.

In yet another embodiment, the present invention relates to a system comprising: a) a loading station from loading at least one vial container in a closed position, the container having an opening at its upper end for containing a liquid and a lid attached to one portion of the upper end of the container by a hinge; b) an orientation device for situating the vial container to a predetermined position in preparation for the lid to be opened; c) a lid opening device for situating the lid to a first predetermined upper limit position; d) a lid pivoting device for opening the lid to a second position to allow transfer of the liquid; e) a lid closing device for closing the lid upper completion of the transfer; and (f) an unloading station for unloading the vial containers.

In another embodiment, the vial container has bar codes and the system has a bar code reader. The system may also comprise a plurality of containers and the container may be placed in a plurality of racks. In yet another embodiment, the vial container has a latch with a aperture and the container has an outwardly projecting post wherein the aperture of the latch fits around the post thereby securing the lid onto the container in a closed position and the system further comprises a latch opening device for separating the latch from the post thereby placing the latch in a closed position. The system may have at least one conveyor.

In still a further embodiment, the present invention provides a method for automatically opening and closing vial lid and transferring the contents of the vial during an open position. The method comprises the steps of: a) loading a vial container onto a conveyer, the vial container having an opening at its upper end for containing a liquid and a lid attached to one position of the upper end of the container by a hinge; b) orientating the container to a predetermined position in preparation for the lid to be opened; c) opening the lid of the vial to a first predetermined upper limit position; d) opening the lid to a second position to allow transfer of the liquid within the container; e) closing the lid of container; and f) unloading the vial container.

BRIEF DESCRIPTION OF THE DRAWING

A more complete appreciation of the present invention and any of the attendant advantages thereof will be readily understood by reference to the following description when considered in connection with the accompanying drawings in which:

FIG. 8 is a top view of the cutting wheels mounted on the c-shaped flange;

FIG. 9 is a side view of the cutting wheels illustrated in FIG. 8;

FIG. 10 is a top view of a second embodiment of an off-line vial pre-scorer;

FIG. 11 is a side view of the off-line pre-scorer illustrated in FIG. 10;

FIG. 12 is a front view of one embodiment of a latch opening device engaging with a vial;

FIG. 13 is a front view of one embodiment of a latch opening device being illustrated without the vial;

FIG. 14 is a sectional view taken along line 14—14 of FIG. 13;

FIG. 15 is a top plan view of one embodiment of a latch opening device;

FIG. 16 is a top plan view of one embodiment of a latch opening device and the vial;

FIG. 26 is a perspective view of one embodiment of a vial inspection and orientation device.

Figure 1:
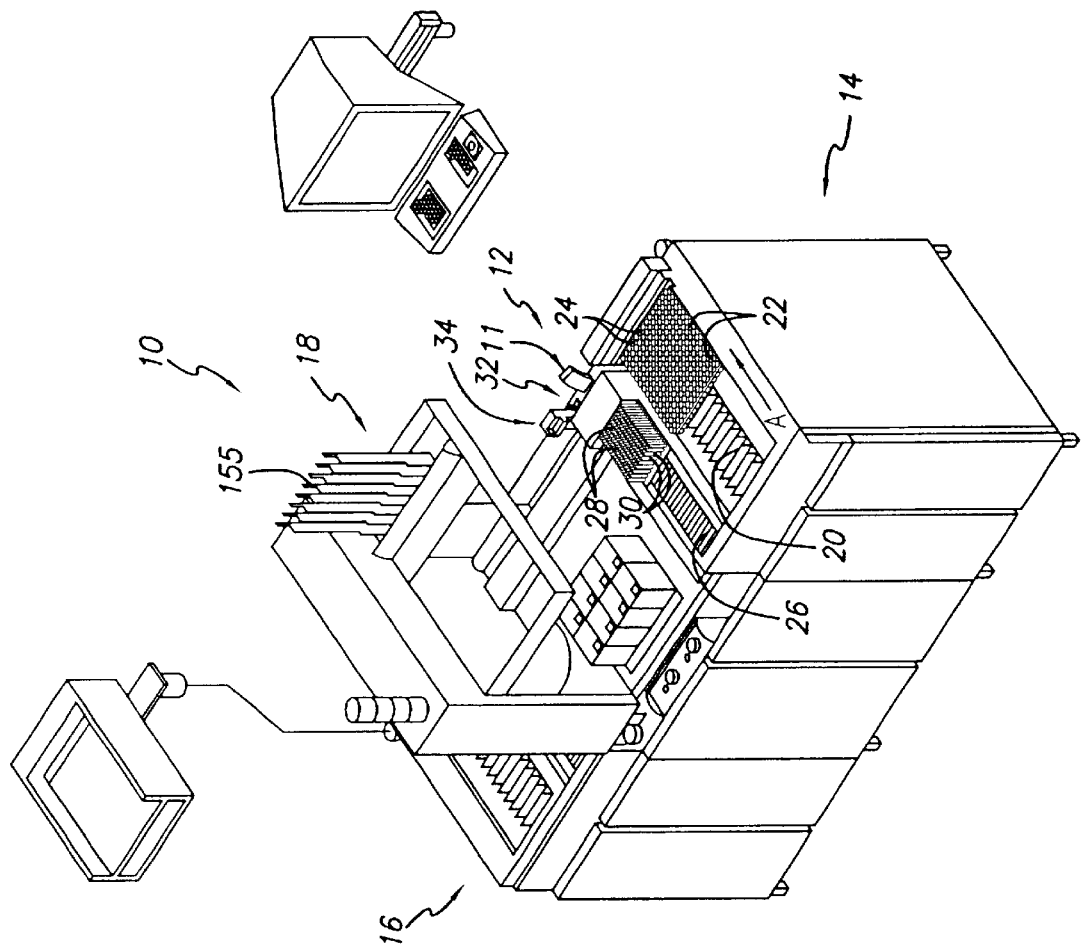
FIG. 1 is a top perspective view of one embodiment of an apparatus for automatically opening and closing vial lids.

DETAILED DESCRIPTION OF THE INVENTION:

Referring now to FIG. 1, an apparatus 10 for automatically opening and closing sample vial lids so that liquid contained therein can be removed from the sample vials and placed in test vials is illustrated. Apparatus 10 includes a device for automatically opening and closing the test vials 12, a load buffer 14, an unloading buffer 16, and a liquid transfer station 18.

The loading buffer includes a first conveyer 20 for advancing a plurality of sample vial racks 22, each rack accommodating one or more sample vials 24. Loading buffer 14 also includes a second conveyer 26 for advancing a plurality of testing vial racks 28, each rack accommodating one or more testing vials 30. Racks 22, 28 advance in the direction indicated by arrow A in FIG. 1. The forward most rack along each conveyor 20, 26 is then advanced, in a conventional manner, in the direction indicated by arrow B. Sample racks 22 preferably move in the direction indicated by arrow B in an incremental or indexing manner. The incremental or index distance is preferably equal to the center to center distance between adjacent vials 24. The rack 28 of test vials can be moved along a separate conveyor in the direction of arrow B to the transfer station 18. Rack 28 will stop at the transfer station 18 until liquid is transferred from the sample vials 24 to the test vials 30. The rack of test vials can be forwarded, either manually or by a conveyor, such as the unloading buffer, to a testing station (i.e., an analyzer) to be tested in a conventional manner.

As the sample vials 24 are indexed from the loading buffer 14 and, before being received at liquid transfer station 18, they first pass through opening stationing 12. Opening station 12 includes a latch opening device 32 and a vial lid opening device 34, which are also illustrated in FIG. 3.

Figure 2:
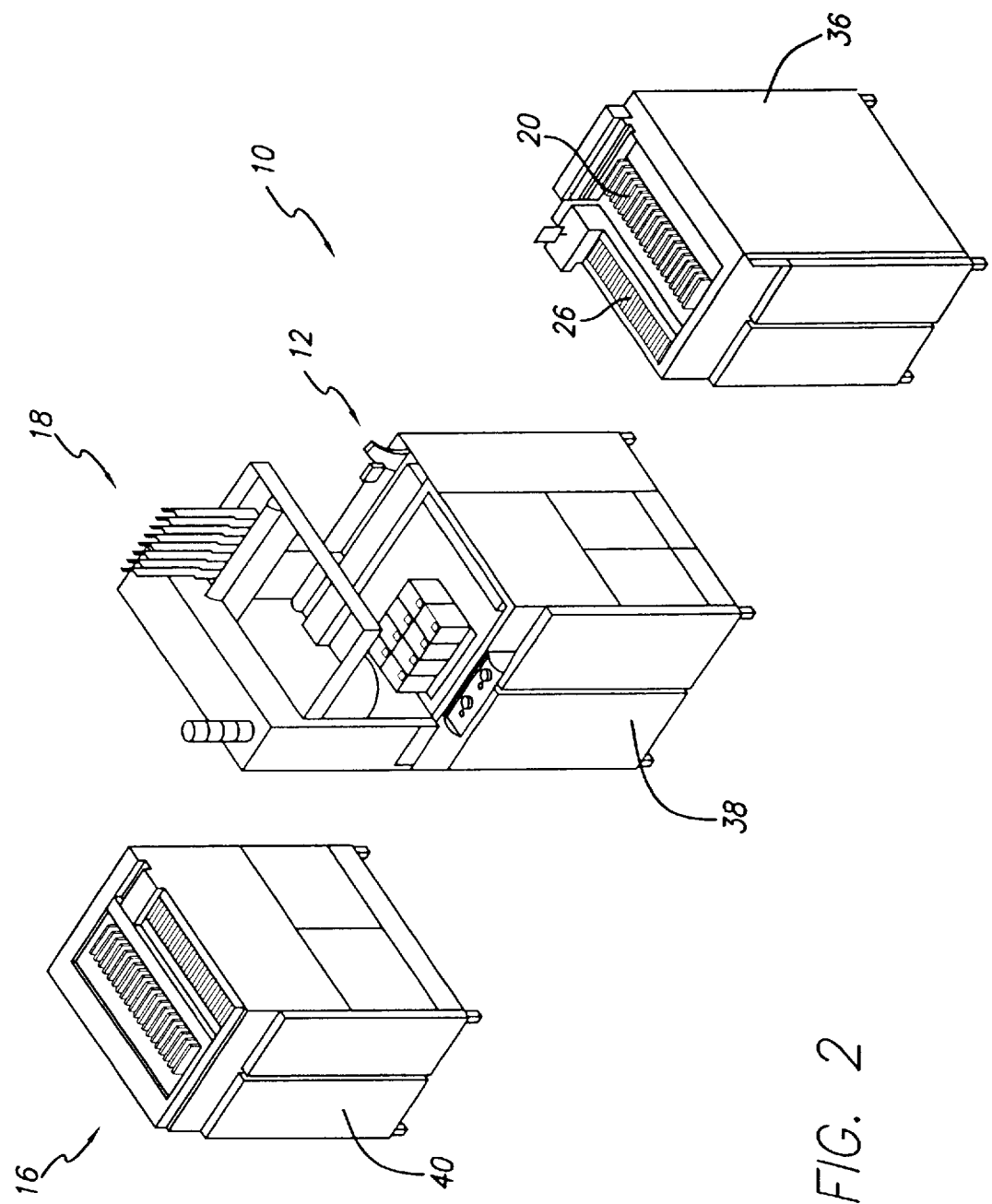
FIG. 2 is a perspective view of one embodiment of an apparatus for automatically opening and closing the vial lids, with the apparatus separated into three separate modules that are selectively connected together.

Referring now to FIG. 2, apparatus 10 as illustrated being divided into three separate modules 36, 38, 40. First module 36 includes the loading buffer module that contains the first conveyer 20 and the second conveyer 26. Second module 38 includes a sample test rack bar code reader, a vial height and orientation device 31, the opening station 12, and the liquid transfer station 18. The third module 40 includes the unloading buffer 16.

Figure 3:
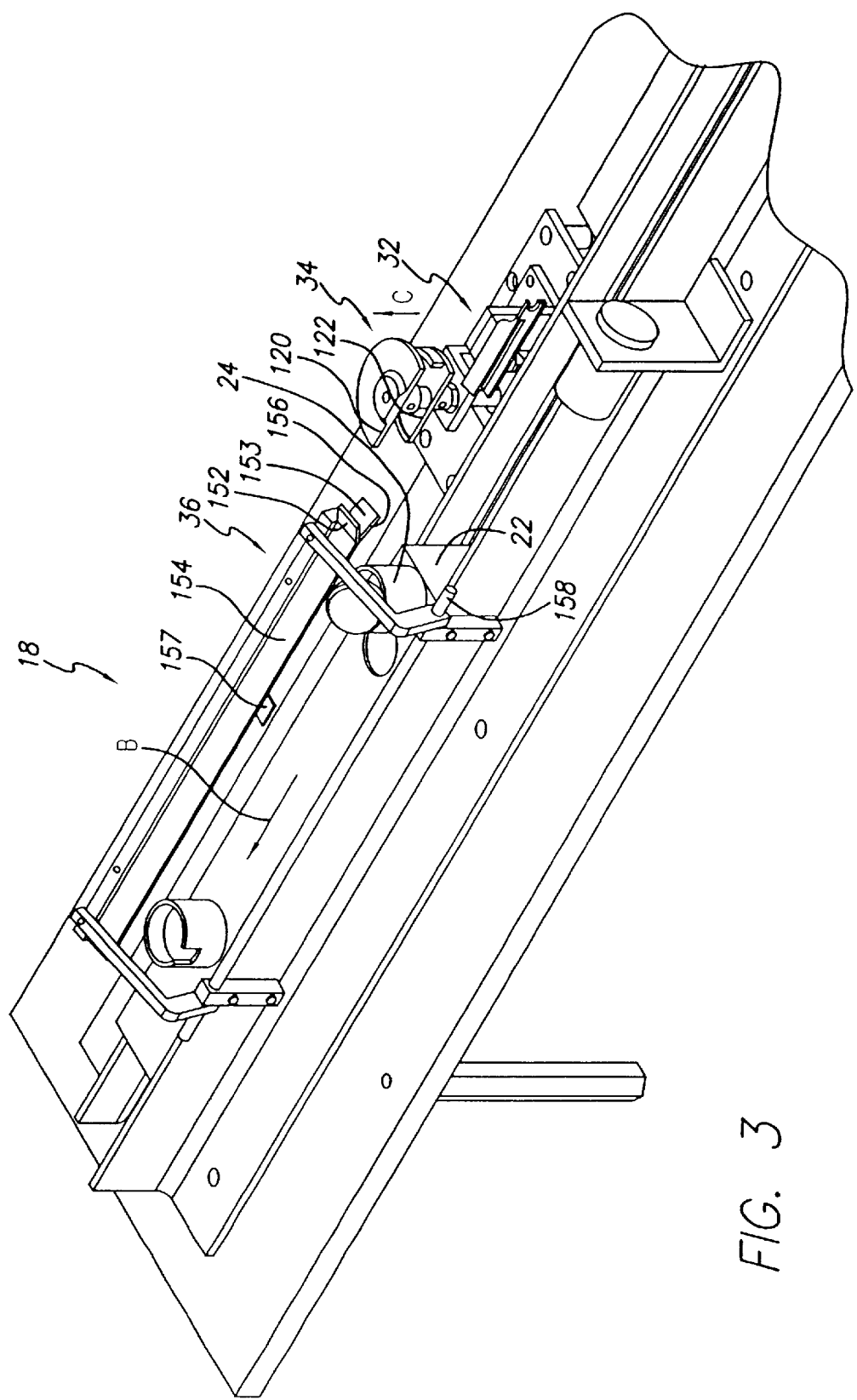
FIG. 3 is a perspective view of one embodiment of a latch opener, vial lid opener and lid pivoting device.

Referring now to FIG. 3, the latch opener 32, the vial lid opener 34, and a lid pivoting device 36 are illustrated. The sample vials 24 each have a tamper evident tape applied over the top surface of the lid and the ends of the tape are pressed down against the outer sidewalls 112 of vial 24. However, the tape is preferably pre-scored adjacent to the juncture of the lower edge of the downwardly depending flange of the lid 92 and the upper end of a flange 264 disposed on the outer cylindrical wall 112 of the vial 24 (see FIG. 24).

Figure 4:
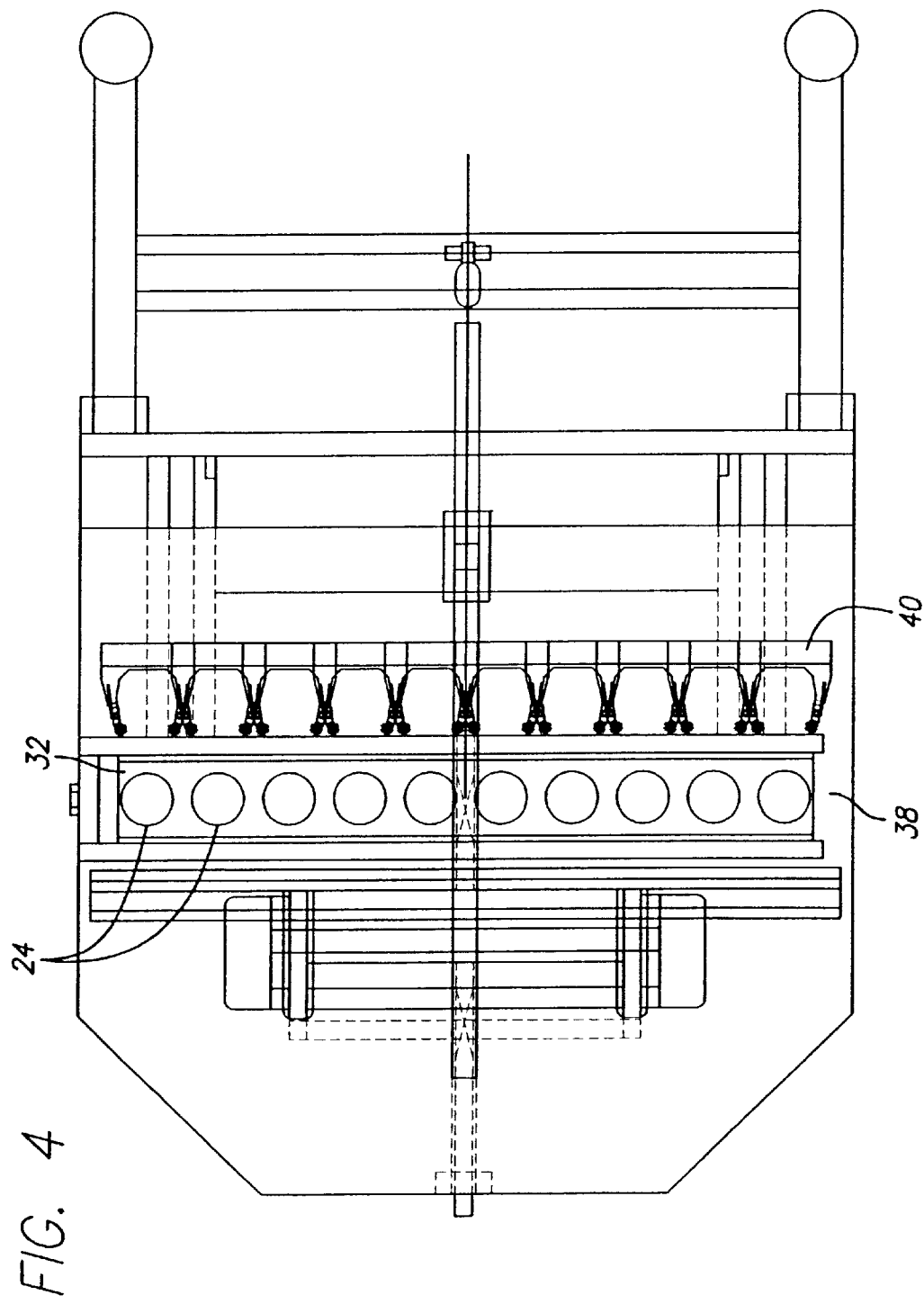
FIG. 4 is a top plan view of one embodiment of a pre-scorer for vials contained in a rack, with the cutting wheels being illustrated in a retracted position.

Referring now to FIGS. 4, 5, 6 and 7, one embodiment of an off-line pre-scorer for the vials 24 that have been placed in a rack 22 is illustrated. Referring now to FIG. 4, rack 22 is illustrated holding ten vials 24. Rack 22 is mounted on a platform 38. A frame 40 is slidably mounted on platform 39.

Figure 5:
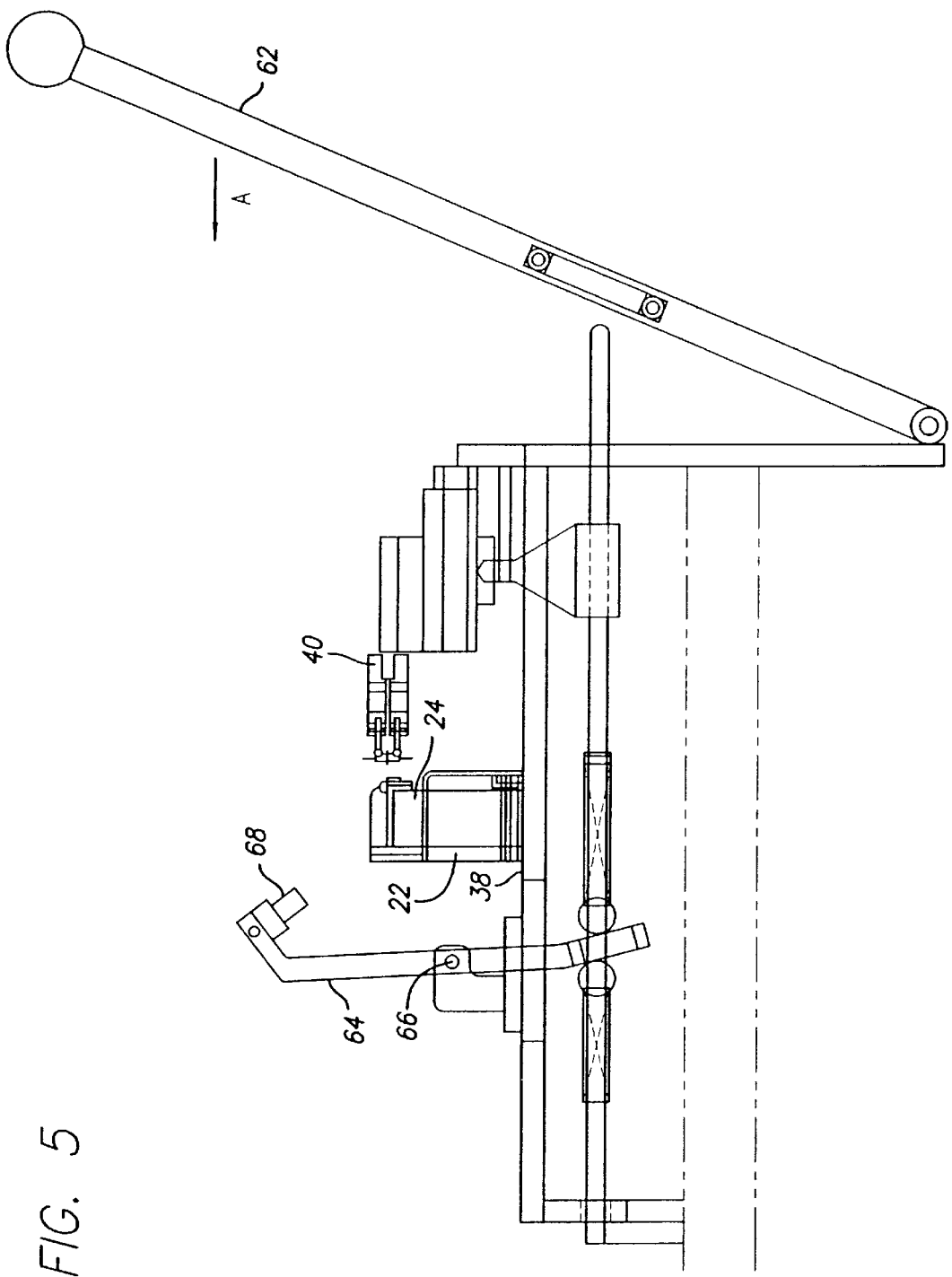
FIG. 5 is a side view of the pre-scorer illustrated in FIG. 4.
Figure 6:
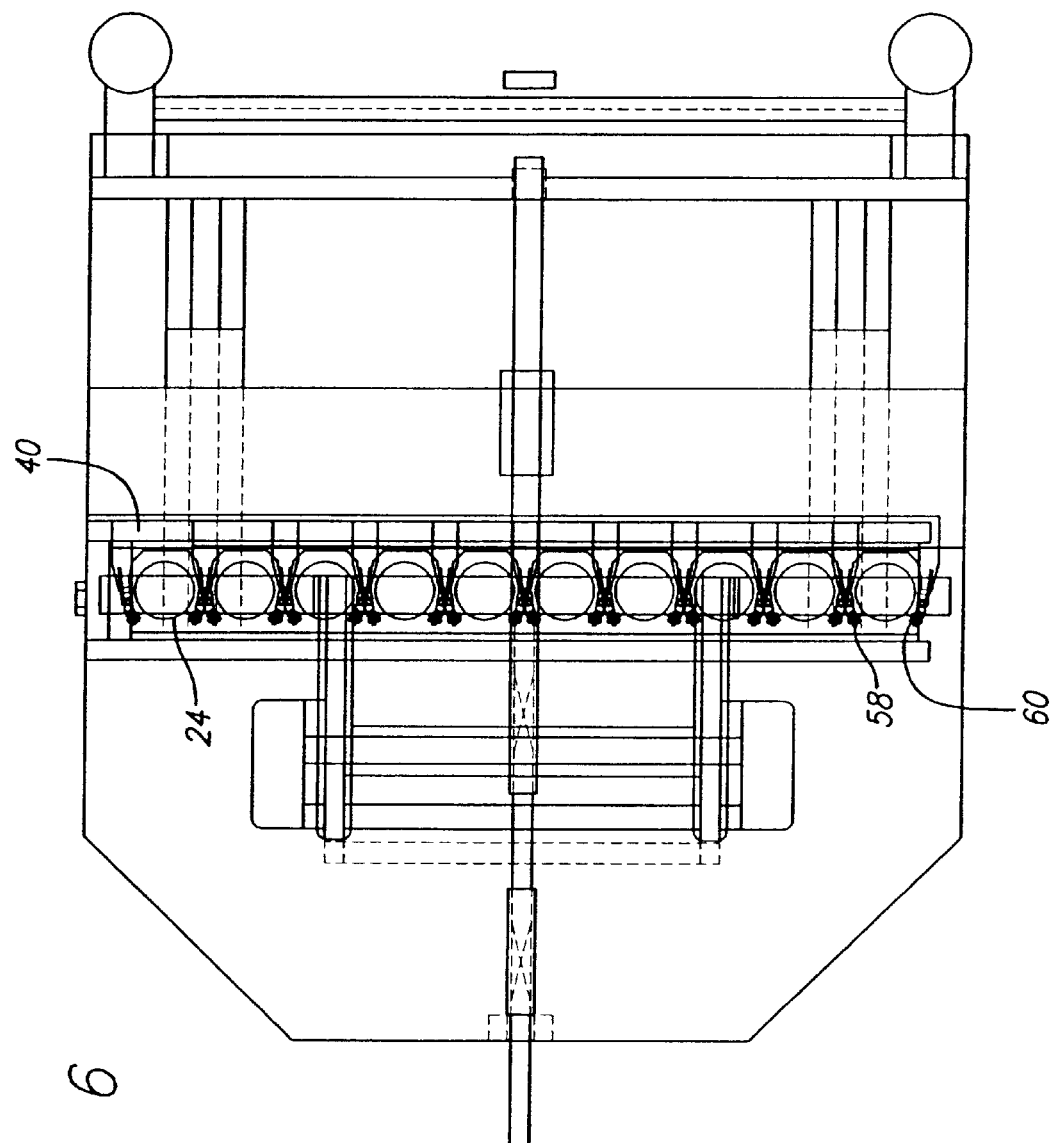
FIG. 6 is a top view of the pre-scorer illustrated in FIG. 4, with the cutting wheels illustrated in the extended position.
Figure 7:
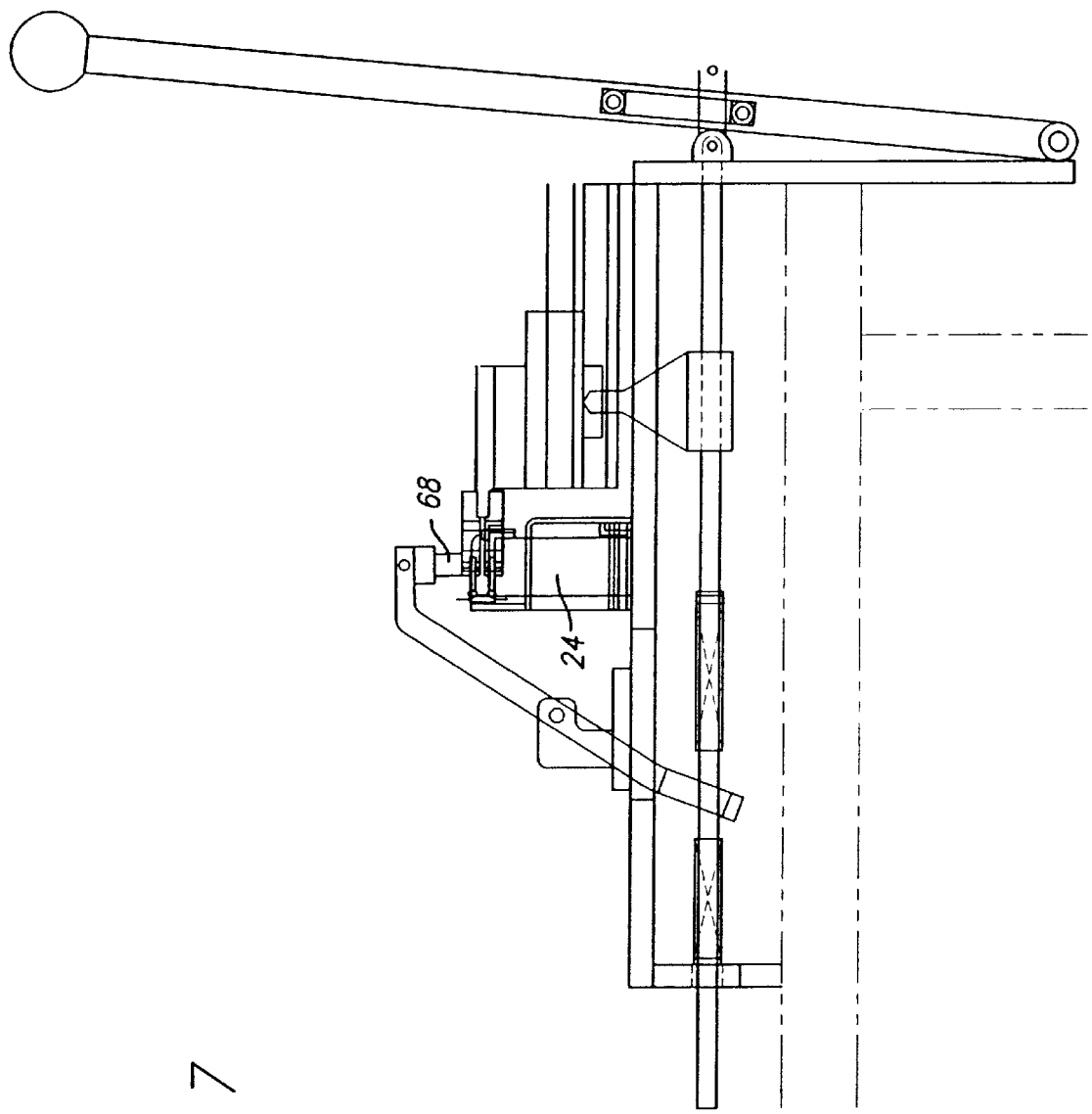
FIG. 7 is a side view of the pre-scorer illustrated in FIG. 6.

Frame 40 moves linearly between a retracted position illustrated in FIGS. 4 and 5 and an extended position illustrated in FIGS. 6 and 7. Referring now to FIGS. 8 and 9, a top view and side view, respectively, of the cutting wheels are illustrated. To score the tape that is placed on each vial, one cutting assembly 42 is used to score both sides of the tape. Assembly 42 includes a c-shaped frame 44 to which a pair of cutting wheel mounting arms 46, 48 are pivotally mounted about pivot pins 50, 52, respectively. A leaf spring 54, 56 is used to bias respective arms 46, 48 towards each other. Cutting wheels 58, 60 have a serrated periphery and are freely rotatably mounted at the distal end of arms 46, 48 respectively.

FIGS. 5 and 7 illustrate another embodiment where a manual actuation handle 62 for reciprocating frame 40 is illustrated. Handle 62 is movable from the retracted position illustrated in FIG. 5 and is pivoted in the direction indicated by arrow A in FIG. 5 to the extended position illustrated in FIG. 7 thereby causing frame 40 to move towards rack 22. Simultaneously, actuation of handle 62 causes arm 64 to pivot about pine 66, thereby causing the distal end 68 of arm 64 to engage the top surface of the lid 92 of vial 24. Distal end 68 preferably engages the top surface of the vial lid 92 before the cutting wheels 58, 60 engage the outer cylindrical surface of the vial 20, 24. Additionally, distal end 68 does not lift off of id 92 until after the cutting blades 58, 60 have moved rearwardly to a position where they are no longer in contact with the outer cylindrical surface 112 of vial 24. Of course, the movement of frame 40 and arm 64 can be effected automatically (e.g., by stepper motor) in a manner known to those skilled in the art. Additionally, the movement of frame 40 can be detected by position limit sensors, which feed their respective signals to a conventional control system.

In operation, as frame 40 is moved from the retracted position to the extended position, cutting wheels 58, 60 engage the outer cyclindrical surface 112 of vial 24 in the area adjacent to the juncture of the lid of the container and the upper end wall of the container. The leaf springs sufficiently bias the cutting wheels into the container thereby effectively scoring the tape without damaging the vial. The cutting wheels 58, 60 cut through the tape during both the forward and backward pass about vials 24. Thus, the cutting wheels 58, 60 effectively prescore the tape that has been placed about the top surface of the lid and down each side surface of the vial. The rack 22 containing the prescored vials is placed in the loading buffer 20 in any manner known to those skilled in the art (e.g., the racks can either be manually or automatically fed to the loading buffer 20).

Referring now to FIGS. 10 and 11, another embodiment of an off-line vial prescorer 70 is illustrated. Prescorer 70 includes an elongated frame 72 that is slidably mounted on platform 74. Rack 22 is fixedly mounted on platform 74. Frame 72 has a plurality of cutter arms 76 that are pivotally mounted thereon about pivot pins 78. Each arm 76 is spring biased by a spring 80 at one distal end of arm 76. A cutting wheel 82 is rotatably mounted at the opposite distal end of arm 76. Cutting wheel 82 freely rotates with respect to arm 76 and may be serrated in a similar manner as cutting wheels 58, 60, which are illustrated in FIG. 8. The cutting wheels freely rotate and are serrated so that the material or the adhesive of the tape does not build up on the cutting wheel. Tape material and/or adhesive build up on the cutting wheel, may render the cutting wheel ineffective. In other words, the cutting wheels will no longer prescore the tape on the vial.

As in the embodiment illustrated in FIGS. 4–9, elongated frame 72 is reciprocally mounted on platform 74 so that frame 72 moves between a retracted position and an extended position. In this embodiment, the arms 76 that are mounted about the same pivot pin 78 are preferably mounted at opposite ends of pin 78 so that, as the cutting wheels 82 pass by the vials 24, the cutting wheels 82 pass vertically over one another. A manual handle 84 is illustrated to actuate the reciprocal movement of frame 72 with respect to platform 74. Frame 72 is illustrated in FIG. 11 in the fully extended position. Handle 84 is connected by a bar linkage 86 to frame 72. To move frame 72 to the retracted position, bar 84 is moved along or pivoted in the direction indicated by arrow A in FIG. 11.

As in the embodiment illustrated in FIGS. 4–9, a downward force may be applied to the top surface of the lid of the container 24 while the cutting wheels 82 are scoring the tape on the outer cylindrical surface of the container 24. This force can be applied by hold down member 88, which, in the illustrated embodiment, is actuated manually by handle 90. Hold down member 88 is in contact with the upper surface of the lid of container 24 during both the forward and rearward pass of the cutting wheel 82 along the outer cylindrical surface of the vial to ensure that the vial is securely maintained in its respective socket in rack 22.

Referring now to FIGS. 3 and 26, one embodiment of a vial height inspection and orientation device 31 is illustrated. Device 31 includes a rotary encoded stepper motor 302 that rotatably drives a cam 304. Cam 304 includes a first notch 306 and a second 308 located 180 degrees apart from one another. Cam 304 is positioned so that when it rotates by 180 degrees it abuts hinge 94 or vial 24. A first optical detector 310 is disposed at a predetermined positioned about cam 304 and a second optical detector 312 is positioned a second predetermined position about cam 304. First sensor 310 detects the position of cam 304 when it has rotated and abutted hinge 94. Sensor 312 detects whether cam 304 has rotated by 180 degrees or not. Vial 24 is seated in a blind bore of rack 22 such that hinge 94 is received in a hinge notch 314. If properly seated, vial 24 will have its hinge 94 located at a predetermined height position, when can be detected by sensor 310 mounted about cam 304. Alternatively, the sensor located on the conventional encoded stepper motor may be used to determine the exact angular orientation of the motor shaft when cam 30 abuts hinge 94. Hinge 94, and thus vial 24, maybe seating too high in rack 22, which can be detected by cam 304. Alternatively, if cam 304 rotates too far this may indicate a misorientation of the vial 24 within rack 22 or that no vial is present. If the sensors detect that the vial has been mis-seated, either too high o too low within rack 22, the indexing can be stopped by a control system, in a manner that is known in the art, and the operator may take the necessary corrections. If the sensors detect that no vial is present, the machine can either be controlled to stop indexing to insert a vial or, the machine may be permitted to simply continue indexing even though no vial is present. Thus, the inspection and orientation device 34 ensures that vial 24 is seated properly in seat notch 314.

Referring now to FIGS. 3 and 12–16, one embodiment of the latch opening device 32 is illustrated. Latch opening device 32 is fixedly mounted to the housing of central module 38. The specimen vials 24 index by the latch opening device 32 as they move along the conveyor in the direction indicated by arrow B (see FIGS. 1 and 3). Referring to FIGS. 11 and 12, each vial 24 includes a lid 92 that is integrally connected to the vial 24 by a hinge 94 (see FIG. 11). A latch 96 is pivotally connected to lid 92 via a living hinge 98 at a position diametrically opposite from hinge 94.

Latch 96 has an open through slot 100 that selectively engages with an outwardly projecting post 102 emanating from the outer cylindrical surface of vial 24. Post 102 includes an enlarged head 104 at its distal end which is slightly larger than the width of slot 100. Thus, when latch 96 is in the closed position, as illustrated in FIG. 12, a predetermined force is required to open latch 96.

FIG. 12 illustrates a front view of the vial 24 as it initially comes into contact with the latch opening device 32. Latch opening device 32 includes a fixed plow 104, Plow 104 is an elongated U-shaped device that has a channel 106 which is sized to receive post 102 thereby permitting vial 24 to pass by latch opening device 32 as it is being indexed in the direction indicated by arrow B. Channel 106 is, in part, defined by an upper projecting finger 110. Fingers 108 and 110 engage between latch 96 and the outer cylindrical surface 112 of vial 24 above and below post 102, respectively. Thus, as vial 24 moves in the direction indicated by arrow B in FIG. 12, fingers 108 and 110 force latch 96 to pivot away from cylindrical surface 112 about hinge 98 so that latch 96 disengages from post 102. Simultaneously, the lower surface of finger 108 helps maintain vial 24 in position within rack 22 by applying a downward force on the upper surface of post 102. Fingers 108 and 110 progressively increase in radial dimension to progressively cause latch 96 to pivot further away from cylindrical surface 112. As latch 96 reaches the forward most portion of plow 104, latch 96 eventually rests on the upper surface 114 of the upper portion of plow 104. In another embodiment, surface 114 is angled, preferably at approximately 23 degrees with respect to the horizontal. Thus, as vial 24 passes by plow 104, latch 96 moves from the closed position to the open position and latch 96 is now ready to be received by the lid opening mechanism 34.

After the vial 24 exits from the latch opening station 32, it immediately enters into the lid opening station 34 (see FIGS. 17–20). As the unlatched vial approaches lid opening station 34, mechanism 34 is in the position illustrated in FIG. 3. Thus, a leading edge 120 of an upper retainer plate 126 and a leading edge 122 of a lower cam 124, which are each substantially planer, are substantially parallel to the direction of the vial moment, which is indicated by arrow B in FIG. 1 and 3. Thus, vial 24 may be removed from the lid opening station 34 by an operator if necessary.

Figure 17:
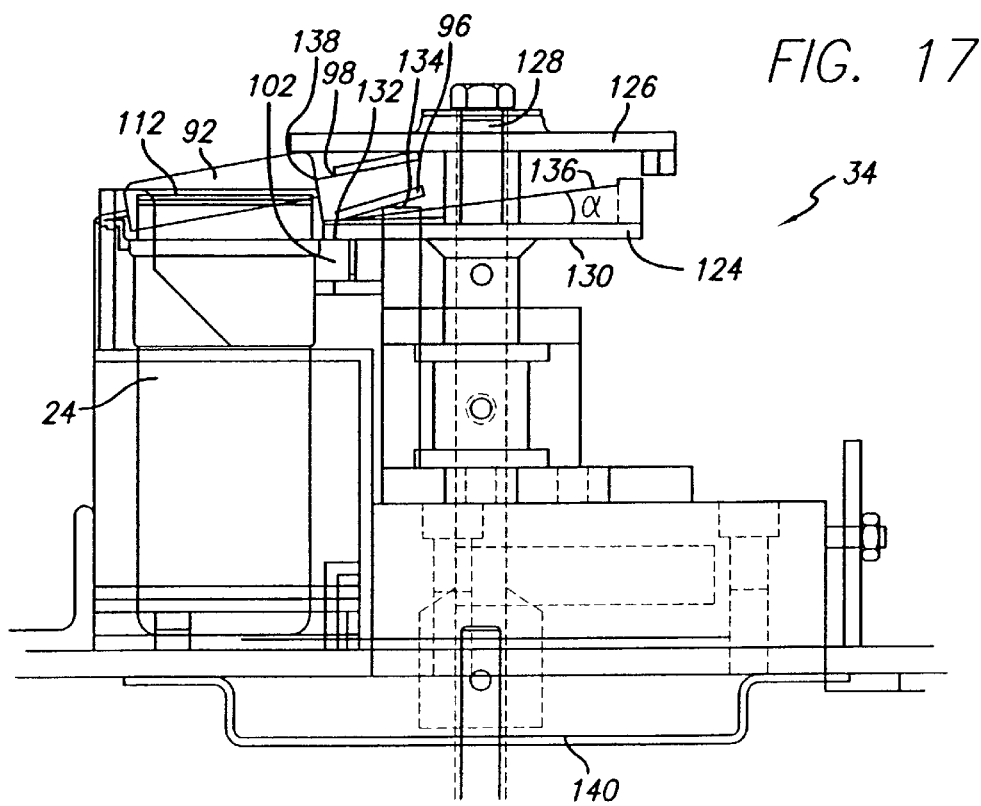
FIG. 17 is a side view of one embodiment of a vial lid opener engaging with the vial.
Figure 18:
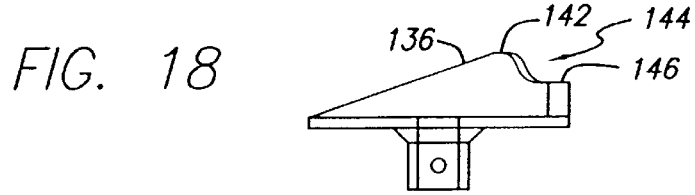
FIG. 18 is a side view of the bottom cam of the lid opening device.
Figure 19:
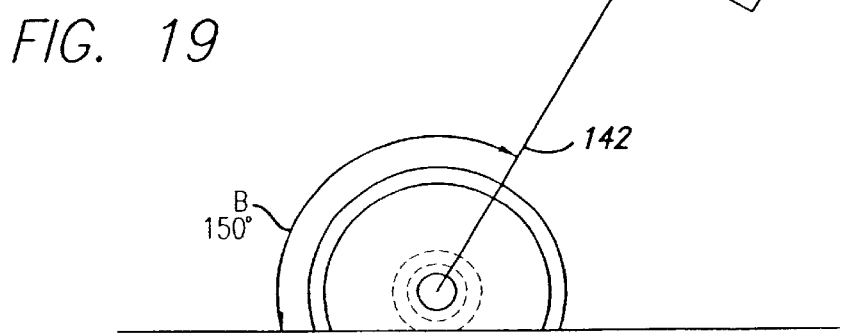
FIG. 19 is a top view of the bottom cam of the lid opening device.

Referring now to FIGS. 17 and 18 that shows one embodiment, vial lid opening device 34 includes a lower cam 124 and an upper retaining plate 126, which are fixed with respect to each other and are rotatably mounted about shaft 128. Opened latch 96 is received between bottom cam 124 and upper retaining plate 126. The lower surface 130 of bottom cam 124 is disposed immediately above the upper surface 132 of post 102 on vial 24. Thus, the lower surface 130 of bottom cam 124 prevents the container portion of vial 24 from lifting upwardly. Vial 24 is indexed to the lid opening station 34 and is then maintained in a stationary position while bottom cam 124 and upper retaining plate 126 rotate together about shaft 128 by 360 degrees (i.e., by one complete revolution). A sensor, may be used to detect if the bottom cam 124 and the upper retaining plate 126 have rotated 360 degrees. If not, the indexing is stopped so that an operator may inspect this station to correct any problems. Thus, the vial lid 92 is opened while the vial is stationary thereby greatly reducing the risk of splashing of the liquid contained within the vial.

As bottom cam 124 rotates, the underneath surface 134 of latch 96 rises on top of upwardly angled cam surface 136. Cam or ramp surface 136 is preferably angled at angle α, with respect to the horizontal, which is approximately equal to 20 degrees. Ramp 136 must rise to a sufficient height to break the hermetic liquid-tight seal between the lid 92 and the container 24, thereby venting the container to the ambient atmosphere. Ramp 136 also must lift the lid to a sufficient height to break the tape that has been placed about the upper surface of lid 92 and down the side cylindrical walls 112 of vial 24. When the lid is being opened, it sometimes has a tendency to open quite abruptly when the hermetic seal and the tape have been broken. The liquid contained within vial 24 may splash out of the vial if the lid is opened too abruptly. Thus, upper retaining plate 126 is positioned above the lid to prevent lid 92 from opening beyond a predetermined upper limit position. This limit position is preferably positioned so that the downwardly depending flange portion 138 of lid 92 only opens by a predetermined minimal gap with respect to the end of the container side wall 112.

Lid opener 34 may be rotatably driven by a stepper motor 140. Depending upon the size of the vial, condition of the vial, the type of tape that is used to provide the tamper-proof seal and whether the tape has been adequately scored, the maximum acceptable force required to open the lid can be determined. The stepper motor can provide feedback to measure the current being applied to the motor. If the current becomes too large, indicating that too large of a force is being applied, the motor can be stopped. If too large of a force is required to open the lid, this could indicate that the tape has been put over the lid in an unusual orientation or was not properly scored, which would require excessive force to open the vial. If this excessive force were permitted to be applied to the lid, sheared lids and/or splashing, all of which may cause cross-contamination of liquid contained in one vial to another vial, may occur. Thus, measuring the force applied to open the lid and limiting that force provides a significant safety feature in the present invention.

At no point during the entire opening process does the lid opener 34 contact the lower internal surface of lid 92 to open the lid thereby significantly reducing the risk of cross contamination.

The height of ramp 136 is sufficient to ensure that the tape score is completely separated between the body of the vial and the lid. One embodiment is illustrated in FIG. 18. Ramp 136 reaches a maximum height at position 142 which corresponds to an angle a which is preferably approximately 150 degrees. At position 142, the lid is typically lifted so that the lower edge of flange 138 is slightly above the upper end of container sidewall 112 to ensure that the tape is completely broken. After the latch 96 passes by position 142, latch 96 rides down ramp 136 along portion 144 to plateau 146. Plateau 146 is of a sufficient height to ensure that the downwardly depending flange of lid 92 overlaps with respect to the upper portion of the cylindrical side wall 112 of vial 24.

Figure 20:
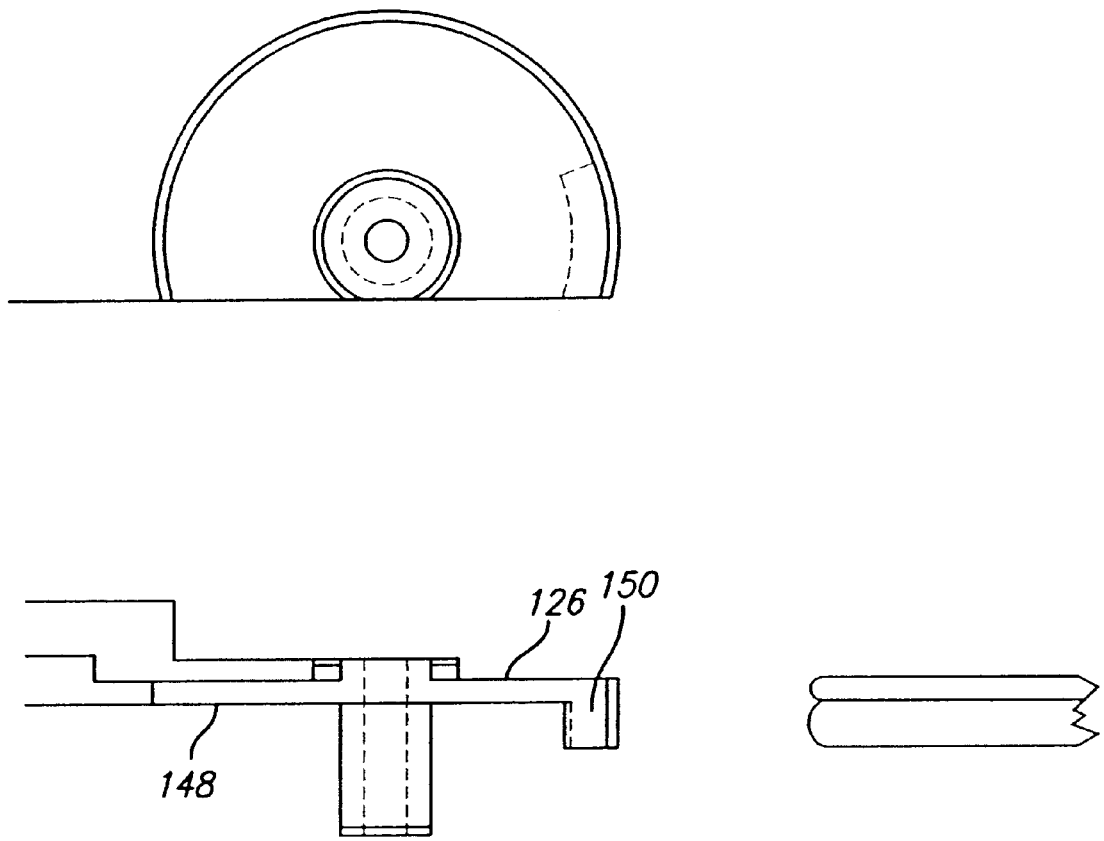
FIG. 20 is a side view of the upper retaining plate of the lid opening device.

Referring now to FIG. 20, the top retaining plate 126 is illustrated. Plate 126 includes a lower surface 148 which limits the upward movement of lid 92 and latch 96 (see FIG. 7). A portion of plate 126 that is disposed above plateau 146 of bottom cam 124 includes a downwardly depending projection 150. Projection 150 pushes lid 92 back down into an overlapping relationship with respect to the container sidewall 112 after the tape score has been completely separated. Thus, vial 24 will not index (i.e., move) away from the lid opening station 34 to the lid pivoting station 36, without lid 92 being in an overlapped position with respect to the container sidewalls 112, thereby significantly reducing the risk of cross-contamination. Thus, while the lid is being opened, thereby equalizing the pressure between the container and the ambient atmosphere, the lid is always substantially maintained in the overlapping condition with respect to the container sidewalls. Thus, a substantial amount of a spraying or atomization effect of the liquid that is contained within the vial is prevented. The opened and vented vial now exits the lid opening station 34 and moves, by indexing, into the lid pivoting station 36.

During the first index movement, latch 96 is captured in a channel 152 of the lid pivoting station 36. Channel 152 is initially fanned out in a V-shape 153, thereby, ensuring that latch 96 is received in channel 152. When eight vials 24 have been received in station 36, the conveyor that moves racks 22 is stopped. The lid pivoting station 36 includes eight (8) sensors 157 (one of which is shown), that determine whether a vial latch is present before and during the pivoting step, thereby preventing aspiration if a vial lid is not pivoted. Channel 152 is then pivoted about pivot rod 158 so that the lids 92 of all eight vials 24 are sufficiently opened, preferably by more than 90 degrees, to permit the liquid transfer station 18, which includes a plurality of pipettes 155 (see FIG. 1), or any other conventional system to transfer liquid from the sample vials to a rack of test vials 28. Conventional test racks contain five or ten test vials. However, the number of vials disposed in rack 28 may vary. After the pipettes 155 have transferred the liquid from the sample vials 24 to the test vials 30, the channel 154 can be actuated back down, so that the lids are once again placed in the overlapped position with respect to vials 24. The test vials are then ready to be tested in a conventional manner.

Figure 21:
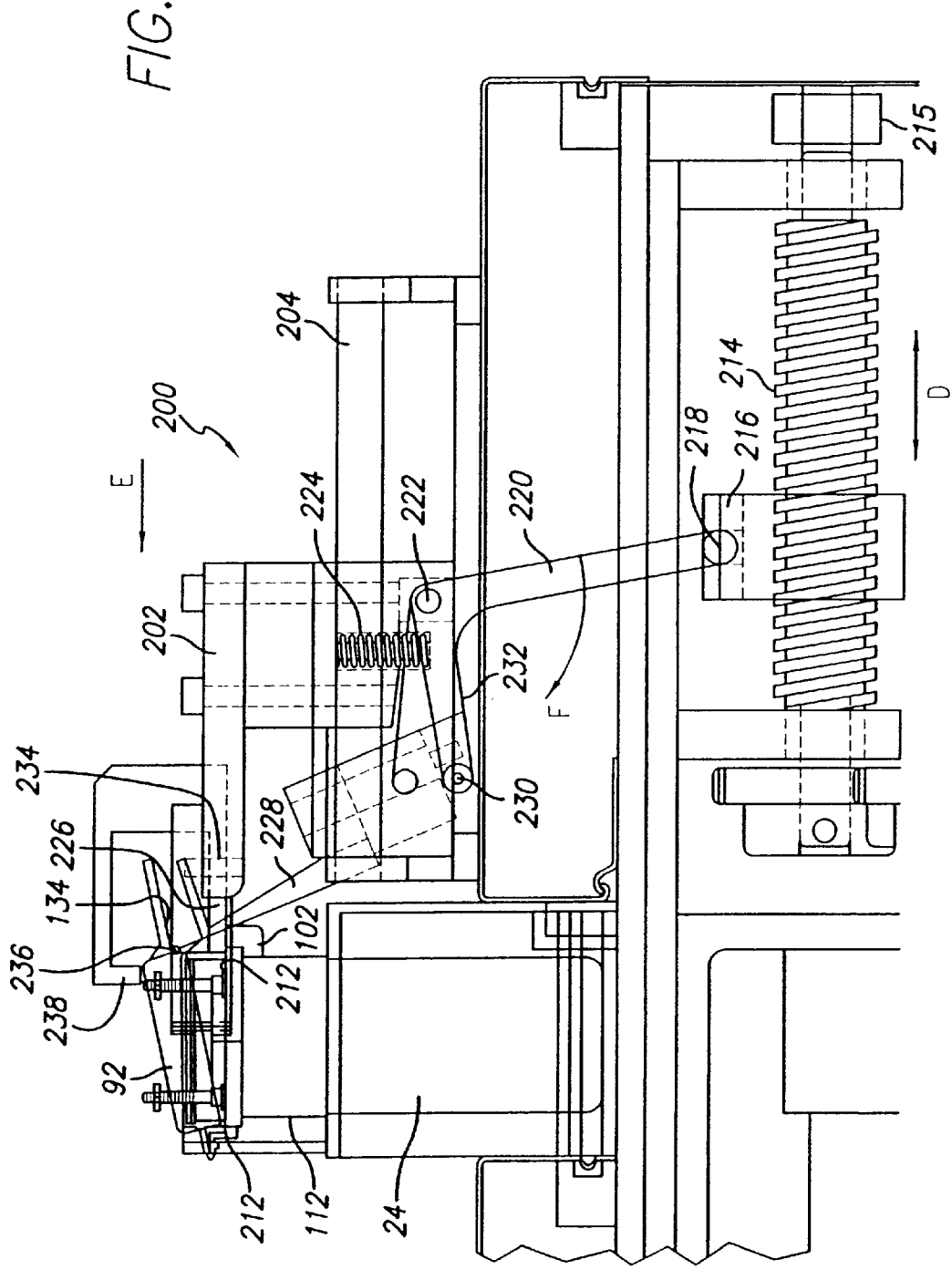
FIG. 21 is a side view of a second embodiment of a vial opening and vial tape scoring device.
Figure 22:
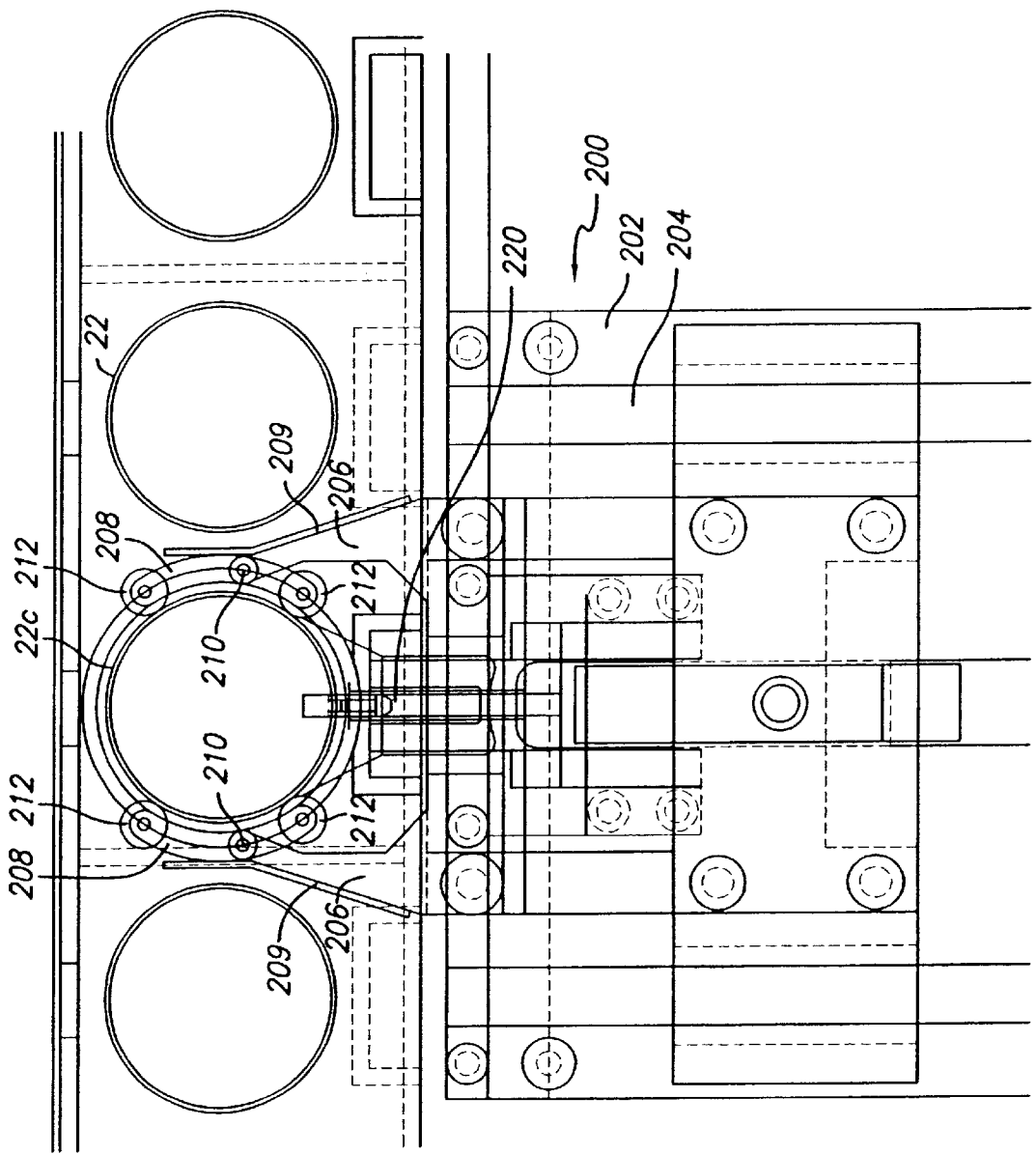
FIG. 22 is a top view of the vial opening and vial tape scoring device illustrated in FIG. 21.

Another embodiment of a vial opening and vial tape scoring station 200 is illustrated in FIGS. 21 and 22. The scorer and lid opener 200 illustrated in FIGS. 21 and 22 eliminates the need for a prescorer. Thus, station 200 substitutes for the lid opening device 34, illustrated in FIG. 3. Vial 24 is indexed to station 200 immediately after passing the latch opening station 32. Station 200 includes a frame 202 that is slidably mounted on fixed guide rods 204. A pair of cutter arms 206 are fixedly mounted to frame 202. A pair of arc-shaped arms 208 are pivotally connected to cutter 206 about pins 210. Arms 208 are biased towards each other by leaf spring 209. Cutting wheels 212 are freely rotatably mounted at each distal end of arc-shaped arms 208. Wheels 212 preferably freely rotate with respect to arms 208 and are serrated in the same manner that cutting wheels 58 and 60 are serrated. Frame 202 is advanced from the retracted position to the engaged position about vial 24 (as illustrated in FIG. 22) by actuation of a threaded rod 214. Rod 214 can be actuated, for example, by a stepper motor 215. An internally threaded block 216 is mounted about rod 214. Thus, rotation of rod 214, about its longitudinal ax, causes threaded block 216 to reciprocate in the direction of the longitudinal axis of rod 214 (i.e., in the direction indicated by arrow D in FIG. 21). Block 216 is pivotally connected about pivot point 218 to an L-shaped arm 220. Arm 220 is pivotally connected to frame 202 about pivot pin 222. Arm 220 is biased in the position illustrated in solid lines in FIG. 21 by coil spring 224. Once frame 202 reaches the position illustrated in FIG. 21, its continued forward or advancing motion, in the direction indicated by arrow E in FIG. 21 is prevented by a stop block (not shown). Thus, further continued rotation of threaded rod 214 causes arm 220 to pivot about pine 222 in the direction indicated by arrow F in FIG. 21. In this position, arms 206 have full extended to the position illustrated in FIG. 22 causing cutting wheels 212 to score the adhesive tape that has been placed about the top surface of lid 92 and down along the sidewalls 112 of container 24. Additionally, a forward projecting tab 226, which is fixedly mounted on frame 202, is now disposed immediately above post 102 of container 24 thereby preventing container 24 from lifting upwardly. A plunger 228 is slidingly connected to a pivot pin 230 that is mounted on the distal end of the second leg 232 of L-shaped arm 220. Thus, the pivoting movement of L-shaped bracket 220 causes plunger 228 to move from the lower limit position 234 to the upper limit position 236 illustrated in FIG. 21. During this upward movement, plunger 228 engages the lower surface 134 of lid 92, thereby opening the lid and completely separating the score in the tape. Lid 92 is prevented from opening beyond the overlapped or substantially overlapped position with respect to the cylindrical sidewalls 112 of the container 24 by an upper stop 238 which is fixedly attached to frame 202. Thus, lid 92 is opened by a sufficient elevation to ensure that the tape score is completely separated between the body of the vial 24 and the lid 92 while also ensuring that the pressure inside the vials equalized with the ambient pressure.

The stepper motor that drives threaded rod 214 is now reversed, thereby causing plunger 238 to move to the retracted position and, thereafter, causing frame 202 to move to the retracted position. Vial 24 can then be indexed to channel 152 of lid pivoting station 36. The next vial 24 is then ready to be indexed into the opener 200.

Figure 23:
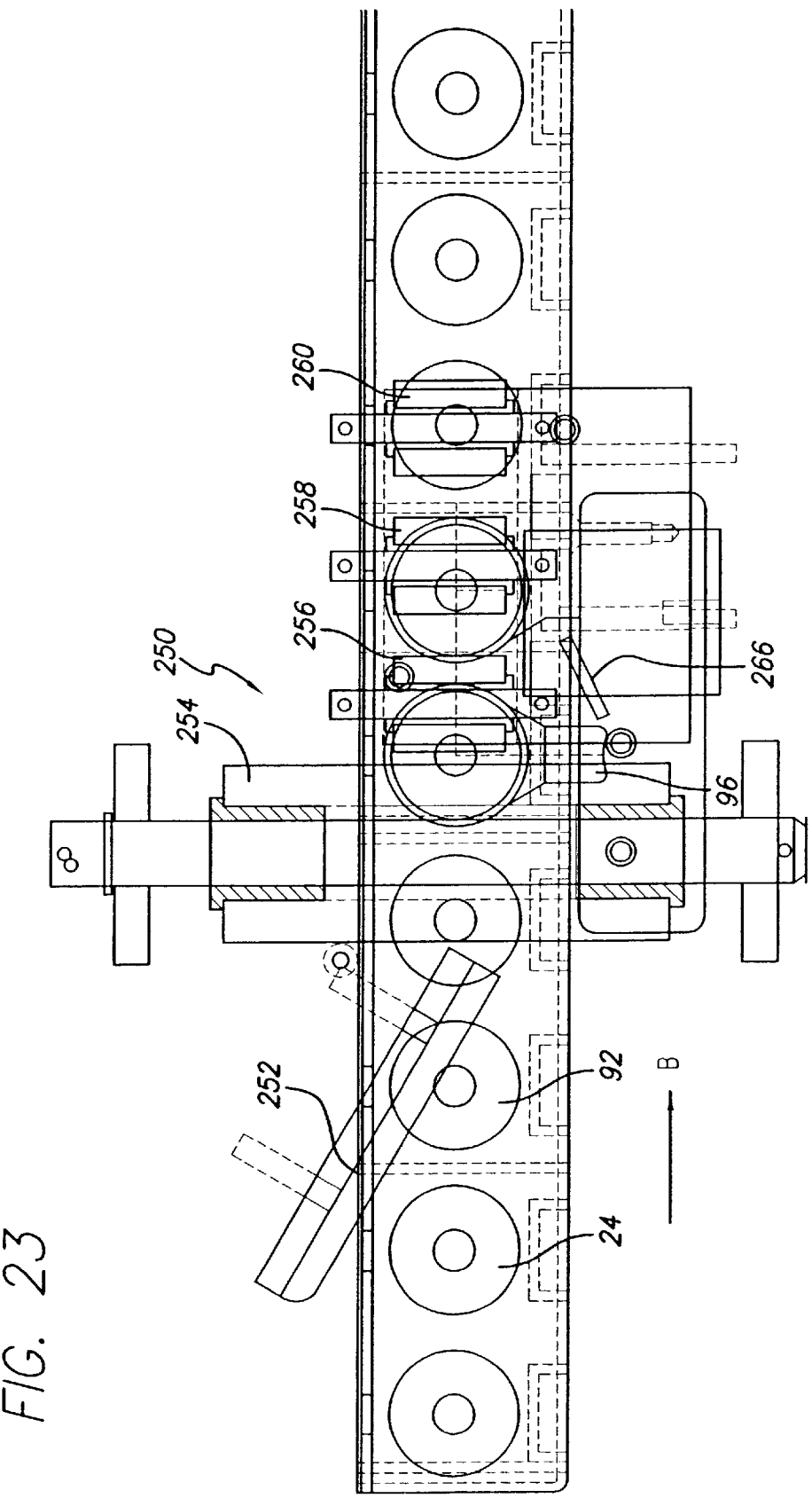
FIG. 23 is a top view of a lid closing station.
Figure 24:
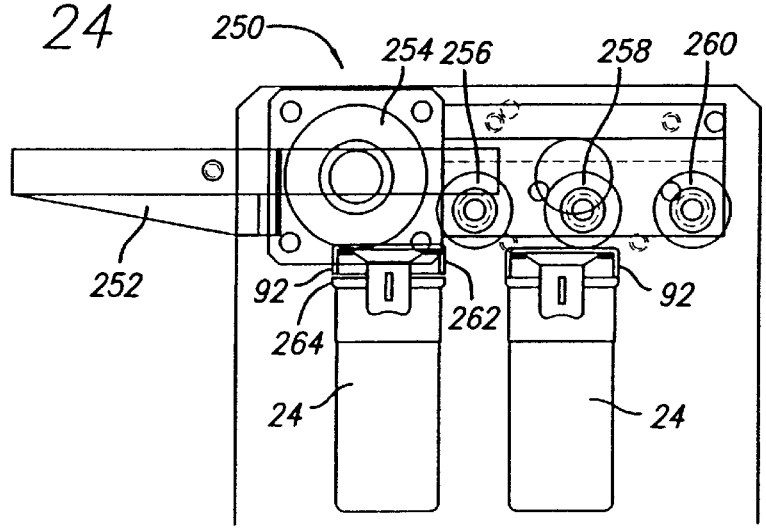
FIG. 24 is a side view of the lid closing station illustrated in FIG. 23.

Referring now to FIGS. 23 and 24, after the vials 24 exit the lid opening station 36, they pass under a lid closing station 250. Lid closing station 250 includes fixed bar 252 that engages with the upper surface of lid 92 and pushes the lid further down upon the vial 24. Bar 252 is disposed above lid 92 and is angled downwardly to force gradually lid 92 further down onto vial 24. To push lid 92 into a hermetically sealed position with respect to vial 24, vial 24 is then indexed underneath a plurality of rollers 254, 256, 258, 260. The lower limit position of each of these rollers progressively lowers with respect to the vial 24. For example, roller 24, as illustrated in FIG. 24, lowers lid 92 to a position just prior to it being snapped into a liquid and air tight sealed position. In other words, there still remains a small gap 262 between the lower surface of lid 92 and the outer flange 264 on vial 24. However, as vial 24 continues to index underneath rollers 256 and 258, lid 92 is forced into a hermetically sealed closed position with respect to vial 24 prior to being conveyed to unloading buffer station 16. In a currently preferred embodiment, bar 252 is angled downwardly, as illustrated in FIG. 24, but not inwardly, as illustrated in FIG. 23. In other words, bar 252 while being inclined downwardly, is aligned with direction that the vials are indexed, as indicated by arrow B in FIG. 23.

Each roller 254, 256, 258 and 260 is biased by a pair of springs 251 in the downward direction. A sensor is mounted on each spring to detect the resistance encountered by each spring. If any spring encounters too much resistance, the sensor will send a signal to a controller to stop the closing procedure. Too large of a resistance indicates that too large of a force than is normally required to close the lid is about to be applied to the lid. Thus, the lid is probably not aligned properly and requires attendance by an operator. Alternatively, a sensor may be mounted on the springs for the first roller only.

Referring now to FIG. 23, it can be seen that latch 96 is pivoted from the unlatched position to the latched position by engaging a fixed bar member 266. Similar to bar member 252, fixed bar member 266 is angled toward the vial to gradually pivot latch 96 from the unlatched position to the latched position.

Figure 25A:
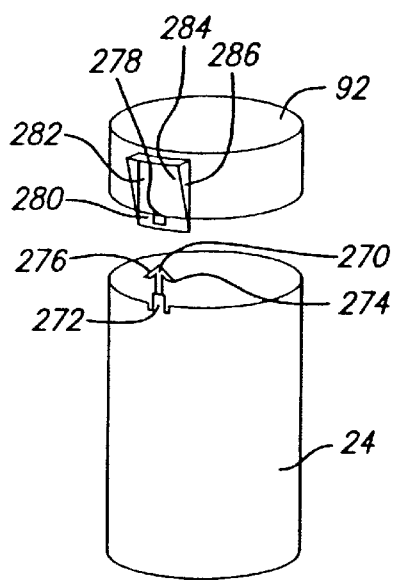
FIG. 25(a) is a perspective view of a vial having a tamper proof safety feature.
Figure 25B:
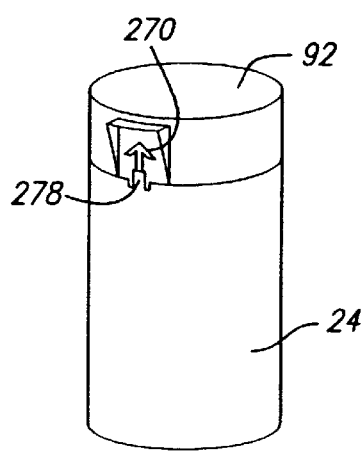
FIG. 25(b) is a perspective view of the vial shown in FIG. 25(a) with the lid being initially closed.
Figure 25C:
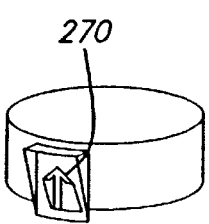
FIG. 25(c) is a perspective view of a vial after it has been opened.

Referring now to FIGS. 25(a)–(c), a further tamper evidence feature is attached to vial 24 and includes an upwardly projecting insertable tab 270, which is preferably arrow-shaped. Tab 270 includes a weakened area 272. Thus, when lid 92 is closed for the first time, the wings 274, 276 bend in towards the stem and are inserted through a slot 278 of an outwardly projecting tab 280 on lid 92. Tab 280 includes walls 282, 284, 286 to prevent access to the two arrow wings 274, 276 after passing through the slot 278.

FIG. 25(b) shows the arrow-shaped tab 270 after it has been initially received in slot 278 upon the initial closing of lid 92. Slot 278 is sized to require the arrow wings 274, 276 to bias towards the stem of the arrow to pass through slot 278. Thus, when lid 92 is opened for the first time (e.g., by the person placing the specimen fluid within the vial, see FIG. 25(c)), wings 274, 276 will not pass through slot 278, but will spread further apart, thereby causing tab 270 to break at the weakened portion 272. Tab 270 is now received within the cup-shaped walls 282, 284, 286 of lid 92 (see FIG. 25(c)), thus, providing evidence that the initial seal of lid 92 has been broken.

Figure 27:
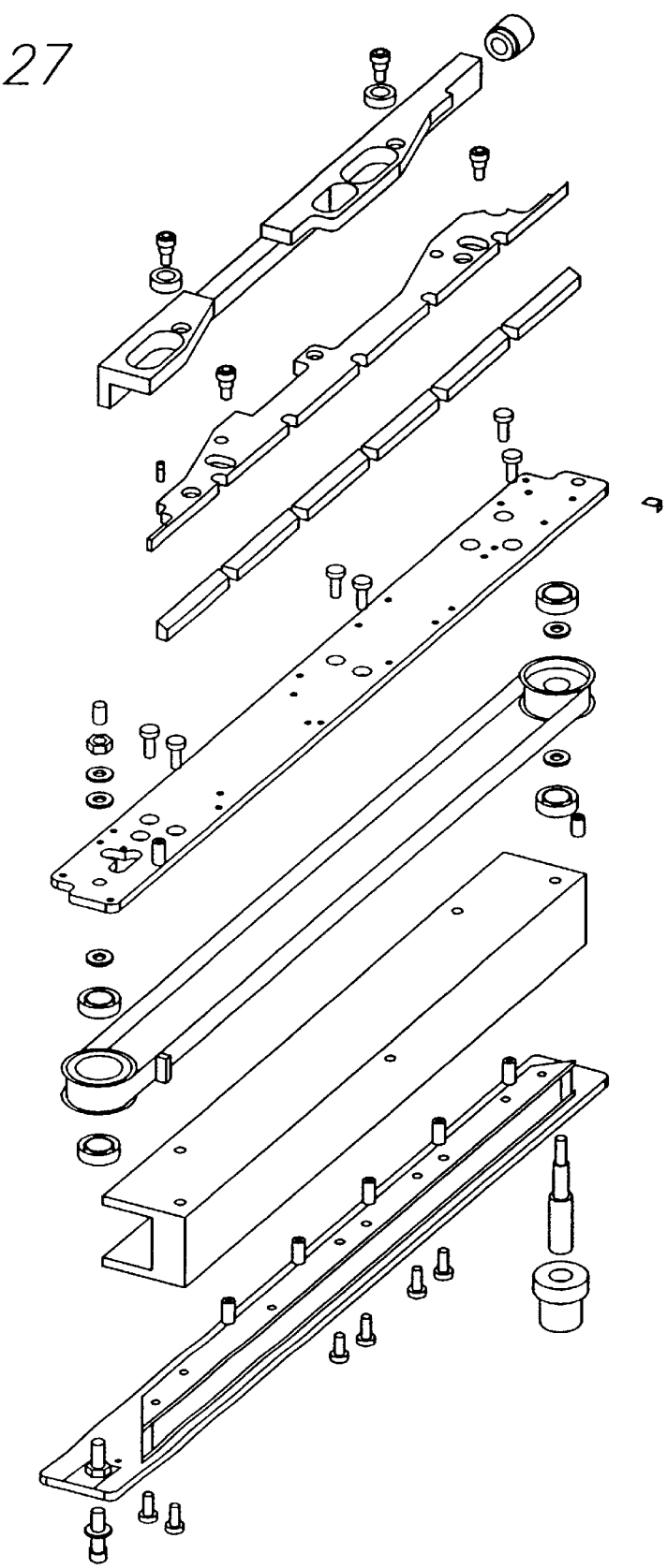
FIG. 27 is a perspective view of the rack brake system of the present invention.
Figure 28:
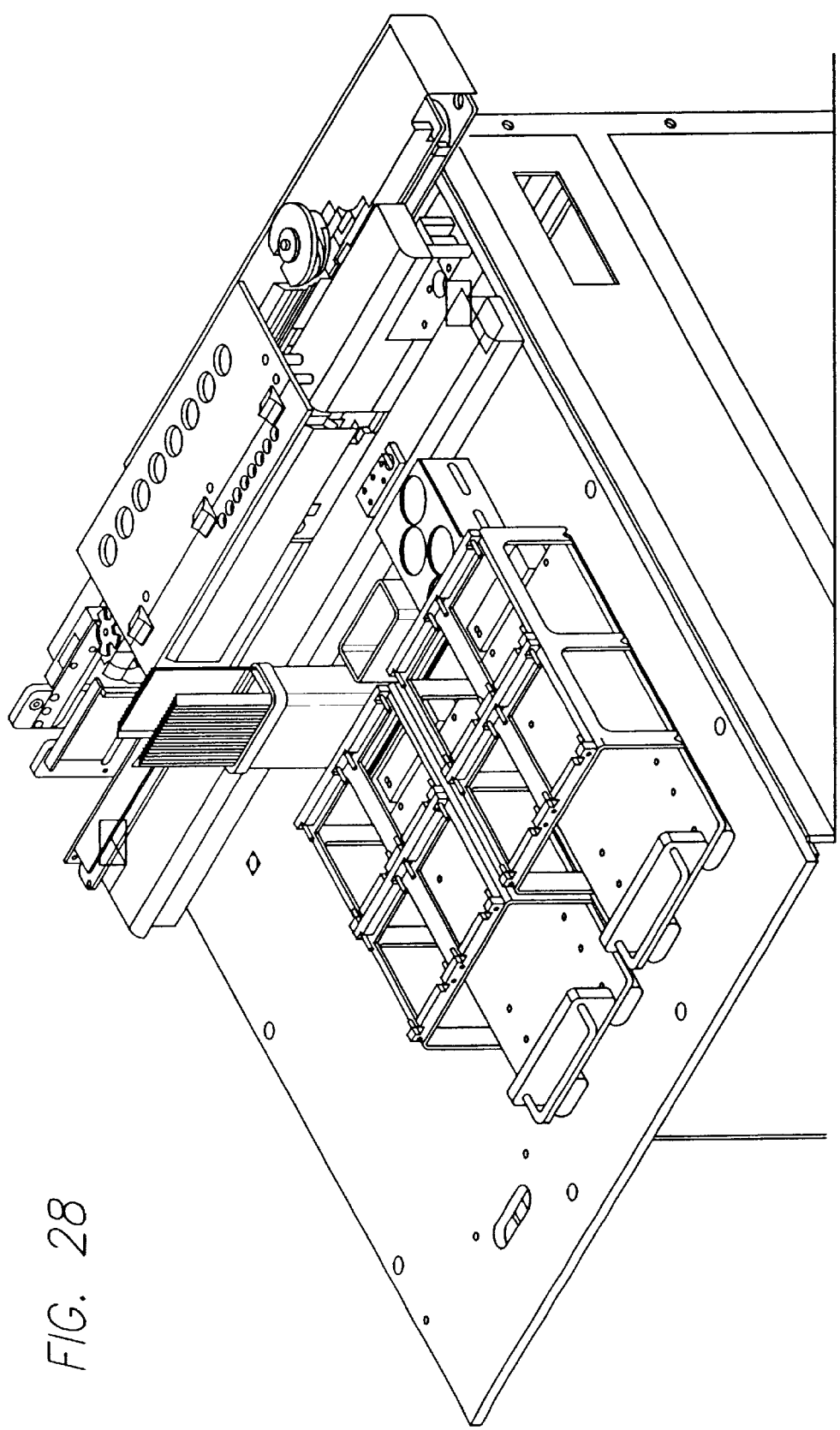
FIG. 28 is a perspective view of the components of the rack brake system.
Figure 29:
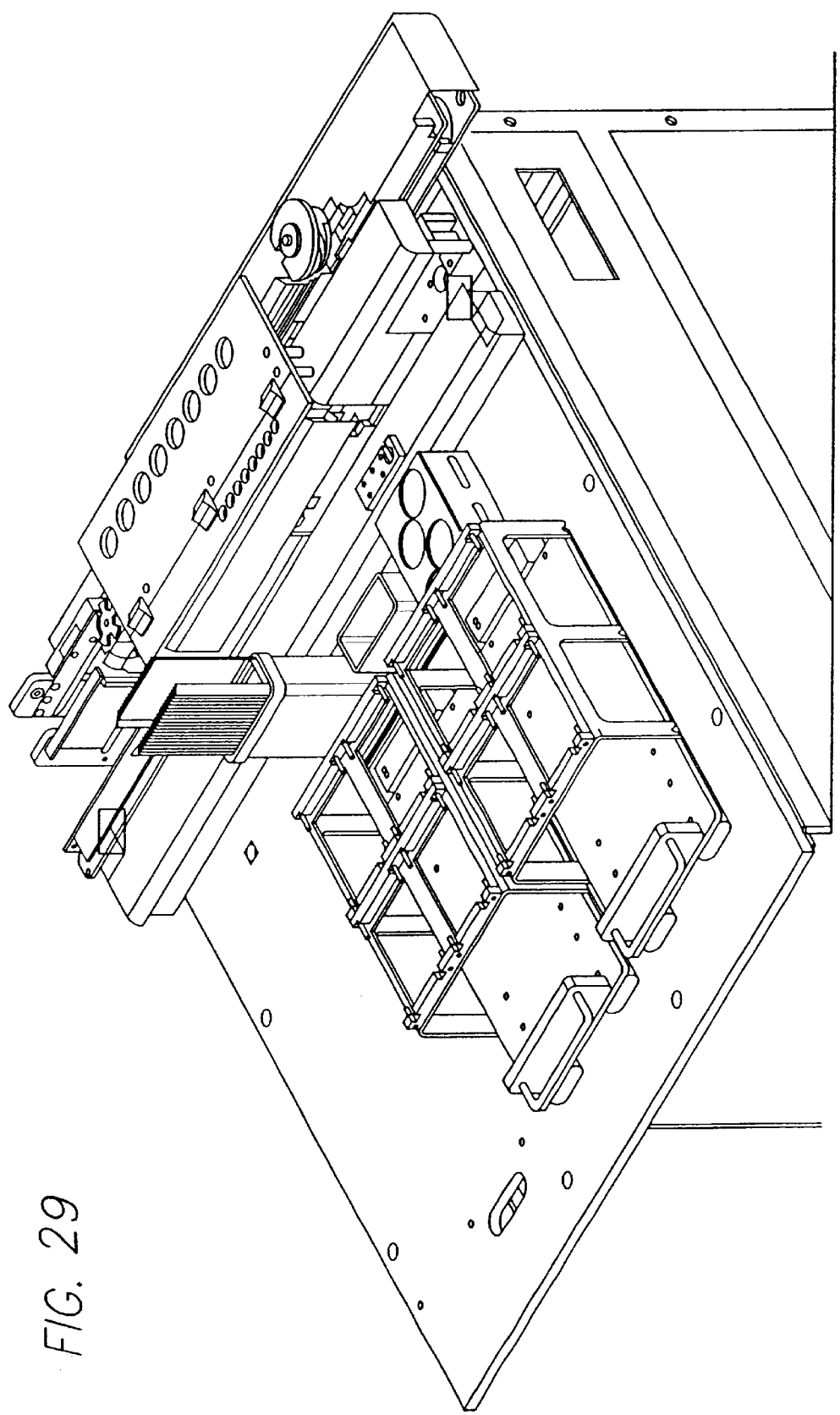
FIG. 29 is a perspective view of the rack brake system in conjunction with the apparatus of the present invention.

Referring now to FIGS. 26–28, the apparatus of the present invention may further comprise a destination rack brake. The rack brake mechanism is used to secure all racks located in the indexing area in the event of user intervention. This mechanism prevents the user from accidentally disturbing the location of the destination tubes by pressing a bar with a closed cell foam strip against the racks. The foam strip engages the various features of the racks and ensures a tight grip.

The rack brake mechanism may consist of a small DC motor which drives a lead screw and which drives a pair of opposing ramps. The combined mechanical advantages of these features allow a small motor to provide enough force to secure the racks in place. The motor is left actuated during the entire engagement period and is designed for continuous duty. To release the brake, the system drives the motor in reverse for a short period of time (e.g., 1 second) then leaves it unpowered.

Numerous modifications and variations of the present invention are possible in light of the above teachings. It is therefore to be understood that within the scope of the attendant clause appended hereto, this invention may be practiced otherwise than as specifically disclosed herein.

What is claimed is:

1. An apparatus which opens the lid of a vial containing a liquid, the vial having a container portion open at its upper end and a lid attached to the upper end of the container by a hinge, the lid having a latch provided with an aperture and the vial having an outwardly projecting post on its upper end, wherein when the vial is received by the apparatus, the lid is closed onto the container and the post is positioned within the latch aperture, wherein the vial is opened by the apparatus, which comprises:
   a) an orienting device for situating the vial container to a predetermined position in preparation of opening the lid of the vial;
   b) a latch opening device for separating the latch of the lid from the post of the vial thereby placing the latch in an opened position;
   c) a lid opening device for opening the lid of the vial; and
   d) a limiter situated above the lid and lid opening device which abuts the lid when the lid is opened the limiter situated at a location that prohibits the lid from opening to a position in excess of a first open position at which the lid overlaps the upper cylindrical end wall of the container.

2. The apparatus of claim 1 further comprising a lid pivoting device for opening the lid of the vial to a second open position to allow transfer of the liquid within the vial container.

3. The apparatus of claim 1 wherein the orienting device comprises a rotatably driven cam, said cam having a first notch located about 180° from a second notch, the cam is positioned so, when said cam rotates by about 180° the cam abuts the hinge of the vial.

4. The apparatus of claim 3 wherein said orientation device comprises at least one optical detector and at least one sensor for determining the position of said cam and to detect whether said cam has rotated about 180°.

5. The apparatus of claim 1 wherein said latch opening device comprises a fixed plow, said plow being an elongated V-shaped device with a channel, said channel being an upper projecting finger and a lower projecting finger, said fingers engaging between the latch and an outer cylindrical surface of the vial container above and below the post, said fingers forcing the latch to pivot away from the cylindrical surface and to disengage from the post.

6. The apparatus of claim 5 wherein the fingers progressively increase in radial dimension.

7. The apparatus of claim 1 wherein the lid opening device comprises a lower cam and the limiter comprises an upper retaining plate, the cam and plate being fixed with respect to each other and rotatably mounted about a shaft, the cam being disposed above an upper surface of the post of the vial, the cam having a ramp which rises in height to break the seal between the lid and the container thereby venting the container, and the plate being positioned above the lid to prevent the lid from opening beyond the first open position.

8. The apparatus of claim 7 wherein the lid opening device is rotatably driven by a stepper motor.

9. The apparatus of claim 1 wherein the lid opening device comprises a channel wherein the latch of vial is captured, the channel being pivoted about a pivot rod thereby allowing the lid to be sufficiently opened.

10. The apparatus of claim 1 wherein the lid opening device comprises at least one sensor for determining the position of the latch of the vial.

11. The apparatus of claim 1 further comprising a lid closing device, said lid closing device comprising a fixed bar for engaging an upper surface of the lid positioned to push the lid down onto the vial container.

12. The apparatus of claim 11 wherein said lid closing device further comprises a plurality of rollers for forcing the lid onto the vial container in a sealed closed position.

13. The apparatus of claim 1 further comprising a cutting assembly for pre-scoring tape adhered to the vial lid, the cutting assembly registering with the vial before the vial enters the orienting device.

14. The apparatus of claim 13 wherein said cutting assembly comprises a c-shaped frame with a pair of cutting wheel mounting arms pivotedly mounted about pivot pins, said arms having a leaf spring and cutting wheels, said cutting wheels having serrated periphery and are rotatably mounted at a distal end of said arms, said cutting wheels prescore the tape at the top surface of the lid and down each said surface of the vial container.

15. The apparatus of claim 13, further comprising a destination rack brake device and a plurality of racks containing a plurality of vials.

16. The apparatus of claim 15 wherein the rack brake device comprises a motor which drives a lead screw which drives a pair of opposing ramps to secure the racks in place.

17. The apparatus of claim 16 wherein the motor is run in reverse to release the brake.

18. The apparatus of claim 1 further comprising a conveyor for moving the vial from the orientation device to the latch opening device to the lid opening device.

19. The apparatus of claim 2 wherein when the lid is in the second open position, a liquid transfer device can be inserted into the open upper end of the container unprohibited by the lid.

* * * * *